(12) United States Patent
Obinata et al.

(10) Patent No.: US 9,522,978 B2
(45) Date of Patent: Dec. 20, 2016

(54) PI POLYAMIDE

(71) Applicant: NIHON UNIVERSITY, Tokyo (JP)

(72) Inventors: Daisuke Obinata, Tokyo (JP); Satoru Takahashi, Tokyo (JP); Kyoko Fujiwara, Tokyo (JP); Satoshi Inoue, Tokyo (JP); Kenichi Takayama, Tokyo (JP)

(73) Assignee: NIHON UNIVERSITY, Tokyo (JP)

( * ) Notice: Subject to any disclaimer, the term of this patent is extended or adjusted under 35 U.S.C. 154(b) by 0 days.

(21) Appl. No.: 14/773,631

(22) PCT Filed: Mar. 11, 2014

(86) PCT No.: PCT/JP2014/056251
§ 371 (c)(1),
(2) Date: Sep. 8, 2015

(87) PCT Pub. No.: WO2014/142092
PCT Pub. Date: Sep. 18, 2014

(65) Prior Publication Data
US 2016/0032057 A1 Feb. 4, 2016

(30) Foreign Application Priority Data
Mar. 11, 2013 (JP) ................................. 2013-048126

(51) Int. Cl.
C08G 73/20 (2006.01)
C07D 405/14 (2006.01)
C07D 403/14 (2006.01)
C07D 519/00 (2006.01)

(52) U.S. Cl.
CPC ............. *C08G 73/20* (2013.01); *C07D 403/14* (2013.01); *C07D 405/14* (2013.01); *C07D 519/00* (2013.01); *C12Q 2525/113* (2013.01)

(58) Field of Classification Search
CPC  C07D 405/14; C07D 519/00; C12Q 2525/113
See application file for complete search history.

(56) References Cited

U.S. PATENT DOCUMENTS

| 7,718,369 B2 | 5/2010 | Tomlins et al. |
| 8,211,645 B2 | 7/2012 | Tomlins et al. |
| 8,541,169 B2 | 9/2013 | Srivastava et al. |
| 8,580,509 B2 | 11/2013 | Tomlins et al. |
| 8,969,527 B2 | 3/2015 | Tomlins et al. |
| 2007/0212702 A1 | 9/2007 | Tomlins et al. |
| 2008/0269157 A1 | 10/2008 | Srivastava et al. |
| 2009/0042965 A1 | 2/2009 | Dervan et al. |
| 2009/0208937 A1 | 8/2009 | Chinnaiyan et al. |
| 2010/0144832 A1 | 6/2010 | Srivastava et al. |
| 2011/0034677 A1 | 2/2011 | Tomlins et al. |
| 2011/0046070 A1* | 2/2011 | Nagase ............... A61K 31/787 514/19.3 |
| 2012/0295809 A1 | 11/2012 | Tomlins et al. |
| 2012/0296070 A1 | 11/2012 | Tomlins et al. |
| 2013/0040858 A1 | 2/2013 | Tomlins et al. |
| 2015/0044670 A1 | 2/2015 | Srivastava et al. |

FOREIGN PATENT DOCUMENTS

| JP | 2009-507492 | 2/2009 |
| JP | 2010-505446 | 2/2010 |
| JP | 2010-532663 | 10/2010 |
| JP | 2011-518552 | 6/2011 |
| JP | 2013-234135 | 11/2013 |
| WO | 2009/066774 | 5/2009 |
| WO | 2009/126122 | 10/2009 |

OTHER PUBLICATIONS

Dose et al., "Next Generation Hairpin Polyamides with (R)-3,4-Diaminobutyric Acid Turn Unit", *J. Am. Chem. Soc.*, vol. 130, pp. 6859-6866, 2008.
Nickols et al., "Suppression of Androgen Receptor-mediated Gene Expression by a Sequence-specific DNA-binding Polyamide", *Proc Natl Acad Sci U.S.A.*, vol. 104, No. 25, pp. 10418-10423, 2007.
Tomlins et al., "Recurrent Fusion of *TMPRSS2* and ETS Transcription Factor Genes in Prostate Cancer", *Science*, vol. 310, pp. 644-648, 2005.
Obinata et al., "Oct1 Regulates Cell Growth of LNCaP Cells and is a Prognostic Factor for Prostate Cancer", *International Journal of Cancer*, vol. 130, pp. 1021-1028, 2012.
International Search Report issued in PCT/JP2014/056251, mailed Jun. 10, 2014.
English translation of the International Preliminary Report on Patentability for PCT/JP2014/056251, mailed Sep. 11, 2015.

* cited by examiner

*Primary Examiner* — Gregory Listvoyb
(74) *Attorney, Agent, or Firm* — Greenblum & Bernstein, P.L.C.

(57) ABSTRACT

To provide a safe and stable medicine useful for prevention and treatment of prostate cancer.
A novel PI polyamide is acquired that recognizes and binds to a specific base sequence of an Oct1 gene binding sequence present in a transcriptional regulatory region (AR response region) of an ACSL3 gene and regulating the transcription activity of AR. This leads to the provision of an ACSL3 gene expression inhibitor and a preventive and/or therapeutic agent of prostate cancer containing the PI polyamide as an active ingredient.

3 Claims, 12 Drawing Sheets

SEQUENCE LISTING

```
<160> NUMBER OF SEQ ID NOS: 22

<210> SEQ ID NO 1
<211> LENGTH: 11
<212> TYPE: DNA
<213> ORGANISM: Homo sapiens

<400> SEQUENCE: 1
tttgcagtat a                                                        11

<210> SEQ ID NO 2
<211> LENGTH: 7
<212> TYPE: DNA
<213> ORGANISM: Artificial sequence
<220> FEATURE:
<223> OTHER INFORMATION: primer

<400> SEQUENCE: 2 wwgcwgw                                                              7

<210> SEQ ID NO 3
<211> LENGTH: 7
<212> TYPE: DNA
<213> ORGANISM: Artificial sequence
<220> FEATURE:
<223> OTHER INFORMATION: Primer

<400> SEQUENCE: 3 wcwgcww                                                              7

<210> SEQ ID NO 4
<211> LENGTH: 7
<212> TYPE: DNA
<213> ORGANISM: Artificial sequence
<220> FEATURE:
<223> OTHER INFORMATION: Primer

<400> SEQUENCE: 4
```

-continued wwwwwgc                                                                7

<210> SEQ ID NO 5
<211> LENGTH: 7
<212> TYPE: DNA
<213> ORGANISM: Artificial sequence
<220> FEATURE:
<223> OTHER INFORMATION: Primer

<400> SEQUENCE: 5 gcwwwww                                                                7

<210> SEQ ID NO 6
<211> LENGTH: 7
<212> TYPE: DNA
<213> ORGANISM: Artificial sequence
<220> FEATURE:
<223> OTHER INFORMATION: Primer

<400> SEQUENCE: 6 wgwwwww                                                                7

<210> SEQ ID NO 7
<211> LENGTH: 7
<212> TYPE: DNA
<213> ORGANISM: Artificial sequence
<220> FEATURE:
<223> OTHER INFORMATION: Primer

<400> SEQUENCE: 7 wwwwwcw                                                                7

<210> SEQ ID NO 8
<211> LENGTH: 8
<212> TYPE: DNA
<213> ORGANISM: Artificial sequence
<220> FEATURE:
<223> OTHER INFORMATION: Primer

<400> SEQUENCE: 8 wcwcgwgw                                                               8

<210> SEQ ID NO 9
<211> LENGTH: 8
<212> TYPE: DNA
<213> ORGANISM: Artificial sequence
<220> FEATURE:
<223> OTHER INFORMATION: Primer

<400> SEQUENCE: 9 wcwcgwgw                                                               8

<210> SEQ ID NO 10
<211> LENGTH: 1140
<212> TYPE: DNA
<213> ORGANISM: Homo sapiens

<400> SEQUENCE: 10
ggcatagtat atctgtggga cattctgtaa acctgtcagt cagtgatacc tacaagcaac      60
cagaattagg ccattttcaa ggcaccttca ttaaagatta aaaggcaacc ttgcctgtcc     120
caaattttac cacacttccc cccaaatgtc accttgtcca gagggaaagg gaaatacgtg     180
attggaaaat ctgctatcat atgcaaactt tacctggaca tgccccactt cttcaaataa     240
agttccactg tgcaaactat tctacggccc tatatcctgc tgtactcatt gttactagaa     300

```
taaatatttg cagtataagc agaactttgt tctgaggata aatccacagg atacttagca    360
ctctgacaaa tgaaaagcca gttttagct gcccttgtt tgatacaaac tggatgttgt      420
gttttctttt ctgggttatg tataacgtac aaattctagg caatctttga caagaactta    480
taataacaaa ctgccttttg acaatgactc tagagagcct tcctgtctcc agaaaatatc    540
cctctgtggc tccaaaggtc tcagtctcag ggtgatgtcc tggctacttt tcttttgcac    600
cataaatgaa atgacagtga agacatcaac ctcgccatgt tggaaaactg cctaagatgt    660
ttcttggaac tgtggccagt cccaggaaca gaaaggcatg atgttcacag ctaaaacttc    720
ctcacagcgg cctgctgtac ctcctcatgc ctgagaattg ctctgaggaa ggactcattt    780
accacatttg cactgcagaa gtcaacaccc agcgatcaaa ggacatcctg gaaaagtcag    840
tatagatcct gaaccaaaaa cctcagaagt gattccaggc tgctgcccaa gagctgacat    900
gcatacattt gttcatcact caacaaatat ttattgagtg ctatctctgt tgtaaacact    960
gtactggatg tgaatgtcca gctgcagaag aaacagaccc aagcctccgg gagctgactg   1020
ttcccaggag ggggcccttg gctctttgca gtgagttgtc atcctgggca ctgacaggca   1080
gtggtgtgag cctgctgagc cagagagacg atgagctgct cccacaatac caataatca    1140
```

<210> SEQ ID NO 11
<211> LENGTH: 34
<212> TYPE: DNA
<213> ORGANISM: Artificial sequence
<220> FEATURE:
<223> OTHER INFORMATION: Primer

<400> SEQUENCE: 11
aaaacgcgtg gcatagtata tctgtgggac attc    34

<210> SEQ ID NO 12
<211> LENGTH: 34
<212> TYPE: DNA
<213> ORGANISM: Artificial sequence
<220> FEATURE:
<223> OTHER INFORMATION: Primer

<400> SEQUENCE: 12
tgaagatctt gattattggg tattgtggga gcag    34

<210> SEQ ID NO 13
<211> LENGTH: 32
<212> TYPE: DNA
<213> ORGANISM: Artificial sequence
<220> FEATURE:
<223> OTHER INFORMATION: Primer

<400> SEQUENCE: 13
tgtaatcatt attactagaa taaatatttg ca    32

<210> SEQ ID NO 14
<211> LENGTH: 28
<212> TYPE: DNA
<213> ORGANISM: Artificial sequence
<220> FEATURE:
<223> OTHER INFORMATION: Primer

<400> SEQUENCE: 14
agaaatttat tctgaggata aatccaca    28

<210> SEQ ID NO 15

-continued

```
<211> LENGTH: 25
<212> TYPE: DNA
<213> ORGANISM: Artificial sequence
<220> FEATURE:
<223> OTHER INFORMATION: Primer

<400> SEQUENCE: 15
taaagttcca ctgtggccct atatc                                              25

<210> SEQ ID NO 16
<211> LENGTH: 27
<212> TYPE: DNA
<213> ORGANISM: Artificial sequence
<220> FEATURE:
<223> OTHER INFORMATION: Primer

<400> SEQUENCE: 16
tagaataaat aagcagaact tgttct                                             27

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
agcagaactt tgttctcagg atactt                                             26

<210> SEQ ID NO 18
<211> LENGTH: 26
<212> TYPE: DNA
<213> ORGANISM: Artificial sequence
<220> FEATURE:
<223> OTHER INFORMATION: Primer

<400> SEQUENCE: 18
gcacaggcgt gttttatgta taattt                                             26

<210> SEQ ID NO 19
<211> LENGTH: 22
<212> TYPE: DNA
<213> ORGANISM: Artificial sequence
<220> FEATURE:
<223> OTHER INFORMATION: Primer

<400> SEQUENCE: 19
caatggctgg acctcctaga gt                                                 22

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
ggtggtctcc tctgacttca aca                                                23

<210> SEQ ID NO 21
<211> LENGTH: 19
<212> TYPE: DNA
<213> ORGANISM: Artificial sequence
<220> FEATURE:
<223> OTHER INFORMATION: Primer

<400> SEQUENCE: 21
```

```
gtggtcgttg agggcaatg                                                   19

<210> SEQ ID NO 22
<211> LENGTH: 5405
<212> TYPE: DNA
<213> ORGANISM: Homo sapiens

<400> SEQUENCE: 22
acgcgtgtat gcttgcactg ctgaatggct gggatgtgtc agggattatc ttcagcactt    60
acagatgctc atctcatcct cacagcatca ctatgggatg ggtattactg gcctcatttg   120
atggagaaac tggctgtggc tcagaaaggg ggaccacta gaccagggac actctggatg    180
ctggggactc cagagaccat gaccactcac caactgcaga gaaattaatt gtggcctgat   240
gtccctgtcc tggagagggt ggaggtggac cttcactaac ctcctacctt gaccctctct   300
tttagggctc tttctgacct ccaccatgat actaggaccc cattgtattc tgtaccctct   360
tgactctatg accccactg cccactgcat ccagctgggt cccctcctat ctctattccc    420
agctggccag tgcagtctca gtgcccacct gtttgtcagt aactctgaag gggctgacat   480
tttactgact tgcaaacaaa taagctaact ttccagagtt ttgtgaatgc tggcagagtc   540
catgagactc ctgagtcaga ggcaaaggct tttactgctc acagcttagc agacagcatg   600
aggttcatgt tcacattagt acaccttgcc cccccaaat cttgtagggt gaccagagca    660
gtctaggtgg atgctgtgca cacggggttt gtgccactgg tgagaaacct gagattagga   720
atcctcaatc ttatactggg acaacttgca aacctgctca gcctttgtct ctgatgaaga   780
tattatcttc atgatcttgg attgaaaaca gacctactct ggaggaacat attgtatcga   840
ttgtccttga cagtaaacaa atctgttgta agagacatta tctttattat ctaggacagt   900
aagcaagcct ggatctgaga gagatatcat cttgcaagga tgcctgcttt acaaacatcc   960
ttgaaacaac aatccagaaa aaaaaggtg ttgctgtctt tgctcagaag acacacagat   1020
acgtgacaga accatggaga attgcctccc aacactgttc agccagagcc ttccacccett  1080 gtctgcagga cagtctcaac gttccaccat taaatacttc ttctgtcaca tcctgcttat   1140
ttatgcctaa ccaaggttct aggtcccgat cgactgtgtc tggcagcact ccactgccaa   1200
acccagaata aggcagcgct caggatcccg aaggggcatg gctggggatc agaacttctg   1260
ggtttgagtg aggagtgggt ccaccctctt gaatttcaaa ggaggaagag gctggatgtg   1320
aaggaactgg gggagggaaa gtgtcagttc cgaactctta ggtcaatgag ggaggagact   1380
ggtaaggtcc cagctcccga ggtactgatg tgggaatggc ctaagaatct catatcctca   1440
ggaagaaggt gctggaatcc tgaggggtag agttctgggt atatttgtgg cttaaggctc   1500
tttggcccct gaaggcaga ggctggaacc attaggtcca gggtttgggg tgatagtaat    1560
gggatctctt gattcctcaa gagtctgagg atcgagggtt gcccattctt ccatcttgcc   1620
acctaatcct tactccactt gagggtatca ccagcccttc tagctccatg aaggtgcccc   1680
tgggcaagca caatctgagc atgaaagatg ccccagaggc cttgggtgtc atccactcat   1740
catccagcat ccacactctg agggtgtggc cagcaccatg acgtcatgtt gctgtgacta   1800
tccctgcagc gtgcctctcc agccacctgc caaccgtaga gctgccgaca tcctcctctg   1860
gtgggagtgg cctgcatggt gccaggctga ggcctagtgt cagacaggga gcctggaatc   1920
atagggatcc aggactcaaa agtgctgagag aatggccata tgtcaccatc catgaaatct   1980
caagggcttc tgggtggagg gcacagggac ctgaacttat gggttttccc caagtctatt   2040
```

```
gctctcccaa gtgagtctcc cagatacgag gcactgtgcc agcatcagcc ttatctccac    2100
cacatcttgt aaaagggact acccagggcc ctgatgaaca ccatggtgtg tacaggagta    2160
gggggtggag gcacggactc ctgtgaggtc acagccaagg gagcatcatc atgggtgggg    2220
aggaggcaat ggacaggctt gagaacgggg atgtggttgt atttggtttt ctttggttag    2280
ataaagtgct gggtatagga ttgagagtgg agtatgaaga ccagttagga tggaggatca    2340
gattggagtt gggttagaga tggggtaaaa ttgtgcttcg gatgagtttg ggattgacac    2400
tgtggaggtg gtttgggatg gcatggcttt gggatgaaaa tagatttgtt ttgatgttgg    2460
ctcagacatc cttggggatt gaactgggga tgaagctggg tttgattttg gaggtagaag    2520
acgtggaagt agctgtcaga tttgacagtg gccatgagtt ttgtttgatg gggaatcaaa    2580
caatggggga agacataagg gttggcttgt taggttaagt tgcgttgggt tgatgggggtc   2640 ggggctgtgt ataatgcagt tggattggtt tgtattaaat tggggttgggt caggttttgg   2700 ttgaggatga gttgaggata tgcttgggga caccggatcc atgaggttct cactggagtg    2760
gagacaaact tcctttccag gatgaatccg gggaagcctt aattcacgtg taggggaggt    2820
caggccactg gctaagtata tccttccact ccagctctaa gatggtctta aattgtgatt    2880
atctatatcc acctctgtct ccctcactgt gcttggagtt tacctgatca ctcaactaga    2940 aacagggga gatttttatca aattcttttt ttttttttt tttttttga gacagagtct    3000 cactctgttg cccaggctgg agtgcagtgg cgcagtctcg gctcactgca acctctgcct    3060
cccaggttca gtgattctc ctgcctcagc ctcctgagtt gctgggatta caggcatgca    3120
gcaccatgcc cagctaattt ttgtattttt agtagagatg gggtttcacc aatgtttgcc    3180
aggctggcct cgaactcctg acctggtgat ccacctgcct cagcctccca aagtgctggg    3240
attacaggcg tcagccaccg cgcccagcca cttttgtcaa attcttgaga cacagctcgg    3300
gctggatcaa gtgagctact ctggttttat tgaacagctg aaataaccaa ctttttggaa    3360
attgatgaaa tcttacggag ttaacagtgg aggtaccagg gctcttaaga gttcccgatt    3420
ctcttctgag actacaaatt gtgattttgc atgccacctt aatctttttt tttttttt    3480 taaatcgagg tttcagtctc attctatttc ccaggctgga gttcaatggc gtgatcacag    3540
ctcactgtag ccttgaactc ctggccttaa gagattctcc tgcttcggtc tcccaatagc    3600
taagactaca gtagtccacc accatatcca gataatttt aaattttttg ggggccggg    3660 cacagtggct cacgcctgta atcccaacac catgggaggc tgagatgggt ggatcacgag    3720
gtcaggagtt tgagaccagc ctgaccaaca tggtgaaact ctgtctctac taaaaaaaaa    3780
aaaaatagaa aaattagccg ggcgtggtgg cacacggcac ctgtaatccc agctactgag    3840
gaggctgagc aggagaatc acttgaaccc agaaggcaga ggttgcaatg agccgagatt    3900
gcgccactgc actccagcct gggtgacaga gtgagactct gtctcaaaaa aaaaaatttt   3960 tttttttt tttgtagaga tggatcttgc tttgtttctc tggttggcct tgaactcctg    4020
gcttcaagtg atcctcctac cttggcctcg gaaagtgttg ggattacagg cgtgagccac    4080
catgactgac ctgtcgttta atcttgaggt acataaacct ggctcctaaa ggctaaatat    4140
tttgttggag aaggggcatt ggattttgca tgaggatgat tctgacctgg gagggcaggt    4200
```

```
cagcaggcat ctctgttgca cagatagagt gcacaggtct ggagaacaag gagtgggggg   4260
ttattggaat tccacattgt ttgctgcacg ttggattttg aaatgctagg gaactttggg   4320
agactcatat ttctgggcta gaggatctgt ggaccacaag atctttttat gatgacagta   4380
gcaatgtatc tgtggagctg gattctgggt tgggagtgca aggaaaagaa tgtactaaat   4440
gccaagacat ctatttcagg agcatgagga ataaaagttc tagtttctgg tctcagagtg   4500
gtgcagggat cagggagtct cacaatctcc tgagtgctgg tgtcttaggg cacactgggt   4560
cttggagtgc aaaggatcta ggcacgtgag gctttgtatg aagaatcggg gatcgtaccc   4620
accccctgtt tctgtttcat cctgggcgtg tctcctctgc ctttgtcccc tagatgaagt   4680
ctccatgagc tacagggcct ggtgcatcca gggtgatcta gtaattgcag aacagcaagt   4740
gctagctctc cctccccttc cacagctctg ggtgtgggag ggggttgtcc agcctccagc   4800
agcatgggga gggccttggt cagcctctgg gtgccagcag ggcaggggcg gagtcctggg   4860
gaatgaaggt tttatagggc tcctggggga ggctccccag ccccaagctt accacctgca   4920
cccggagagc tgtgtcacca tgtgggtccc ggttgtcttc ctcaccctgt ccgtgacgtg   4980
gattggtgag aggggccatg gttggggga tgcaggagag ggagccagcc ctgactgtca   5040
agctgaggct cttccccccc caacccagca ccccagccca gacagggagc tgggctcttt   5100
tctgtctctc ccagccccac tccaagccca taccccagc ccctccatat tgcaacagtc   5160
ctcactccca caccaggtcc ccgctccctc ccacttaccc cagaactttc tccccattgc   5220
ccagccagct ccctgctccc agctgcttta ctaaagggga agttcctggg catctccgtg   5280
tttctctttg tggggctcaa aacctccaag gacctctctc aatgccattg gttccttgga   5340
ccgtatcact ggtccacctc ctgagcccct caatcctatc acagtctact gacttttccc   5400
tcgag                                                              5405
```

PI POLYAMIDE

TECHNICAL FIELD

The present invention relates to a novel pyrrole-imidazole polyamide (hereinafter also referred to as PI polyamide). The present invention more particularly relates to a novel PI polyamide recognizing and binding to a transcriptional regulatory region (AR response region) of an ACSL3 gene that is an androgen response gene and thereby inhibiting the expression of this gene.

BACKGROUND ART

One of steroid hormones, androgen, and a receptor thereof, i.e., an androgen receptor (AR, hereinafter also referred to as AR), are known as being closely involved with proliferation and even canceration of prostate cells.

Therefore, an androgen ablation therapy inhibiting the activity of AR to suppress progression of prostate cancer has been performed as one of the treatment methods of prostate cancer. However, this treatment has a problem that the effect disappears as the treatment proceeds due to a change in characteristics of the prostate cancer cells, making the subsequent treatment difficult.

Since the prostate cancer cells expressing AR show the enhanced expression of androgen response genes, methods such as administering interfering RNA and antisense nucleic acids to the androgen response genes to destabilize the expression of these genes to treat prostate cancer, and administrating an expression vector containing a polynucleotide coding a cytotoxic gene product to cancer cells to treat prostate cancer has been disclosed (Patent Documents 1 to 4).

However the interfering RNA and the antisense nucleic acids are easily degraded and less stable in a living body. In addition, the method including the expression of the cytotoxic gene product in a living body is not considered safe. Therefore, these treatment methods are not considered as adequate methods for treatment of prostate cancer.

Thus, to acquire a stable and safe substance effective for treatment of prostate cancer, the present inventors focused on a PI polyamide sequence-specifically binding to DNA and having high in-vivo stability and high transferability to tissues and cells (Non-Patent Document 1). PI polyamide is a substance composed of aromatic amino acids N-methyl-pyrrole (hereinafter also referred to as Py) and N-methyl-imidazole (hereinafter also referred to as Im).

The present inventors developed a PI polyamide inhibiting expression of a fusion gene between an androgen response gene TMPRSS2 and an ERG gene belonging to the ETS family that is one of the largest families of transcriptional factors (Japanese Patent Application No. 2012-106382). This PI polyamide developed by the present inventors inhibits the expression of the fusion gene between the TMPRSS2 gene and the ERG gene and is also capable of inhibiting the expression of EZH2 gene occurring in association with the expression of this fusion gene. These data indicate that the PI polyamide is useful for prevention, treatment, etc. of prostate cancer.

Additionally, for the purpose of enabling comprehensive prevention, treatment, etc. of prostate cancer, the present inventors attempted in the present invention to develop a useful PI polyimide for an ACSL3 gene that is one of the androgen response genes. While the ACSL3 gene is an androgen response gene related to metabolism of long-chain fatty acid and is known as being highly expressed in prostate cancer, the present inventors have found that the gene enhances the proliferation and the migration ability of prostate cancer cells.

The present inventors found that a transcriptional regulatory region (AR response region) is located 63 kb upstream of the transcription start point of the ACSL3 gene and that two Oct1 gene binding sequences and a GATA gene binding sequence are located as transcription factors in the vicinity of a site at which AR binds to a gene (AR response element, hereinafter also referred to as ARE). The present inventors also found that one of this Oct1 gene binding sequence is a poor-prognosis factor of prostate cancer positively enhancing the transcription activity of AR (Non-Patent Document 2).

Therefore, in the present invention, the present inventors developed a PI polyamide specifically binding to this Oct1 gene binding sequence in an attempt to develop a PI polyamide inhibiting the expression of the ACSL3 gene and therefore useful for prevention, treatment, etc. of prostate cancer.

CITATION LIST

Patent Literature

Patent Document 1: Japanese Unexamined Patent Application Publication (Translation of PCT Application) No. 2010-505446
Patent Document 2: Japanese Unexamined Patent Application Publication (Translation of PCT Application) No. 2011-518552
Patent Document 3: Japanese Unexamined Patent Application Publication (Translation of PCT Application) No. 2009-507492
Patent Document 4: Japanese Unexamined Patent Application Publication (Translation of PCT Application) No. 2010-532663

NON PATENT LITERATURE

Non-Patent Document 1: Tomlins S A et al., Science 310: 644-648, 2005
Non-Patent Document 2: Daisuke Obinata, et al., International Journal of Cancer 130: 1021-1028, 2012

SUMMARY OF INVENTION

Technical Problem

It is a problem of the present invention to provide a safe and stable medicine useful for prevention and treatment of prostate cancer.

Solution to Problem

As a result of intensive studies for solving the problem, the present inventors acquired a novel PI polyamide recognizing and binding to a specific base sequence of an Oct1 gene binding sequence present in a transcriptional regulatory region (AR response region) of an ACSL3 gene and regulating the transcription activity of AR.

In the present invention, the present inventors found that this PI polyamide inhibits the expression of the ACSL3 gene and the AR activity in the transcriptional regulatory region (AR response region) of the ACSL3 gene, and is useful for prevention, treatment, etc. of prostate cancer, thereby completing the present invention.

Thus, the present invention relates to a PI polyamide, an ACSL3 gene expression inhibitor containing the PI polyamide as an active ingredient, and a preventive or therapeutic agent of prostate cancer, as indicated from (1) to (4) below.

(1) A pyrrole-imidazole polyamide binding to the whole or a part of a base sequence indicated by SEQ ID NO:1.

(2) The pyrrole-imidazole polyamide of (0.1) represented by any of following Formulas 1 to 3.

[Formula 1]

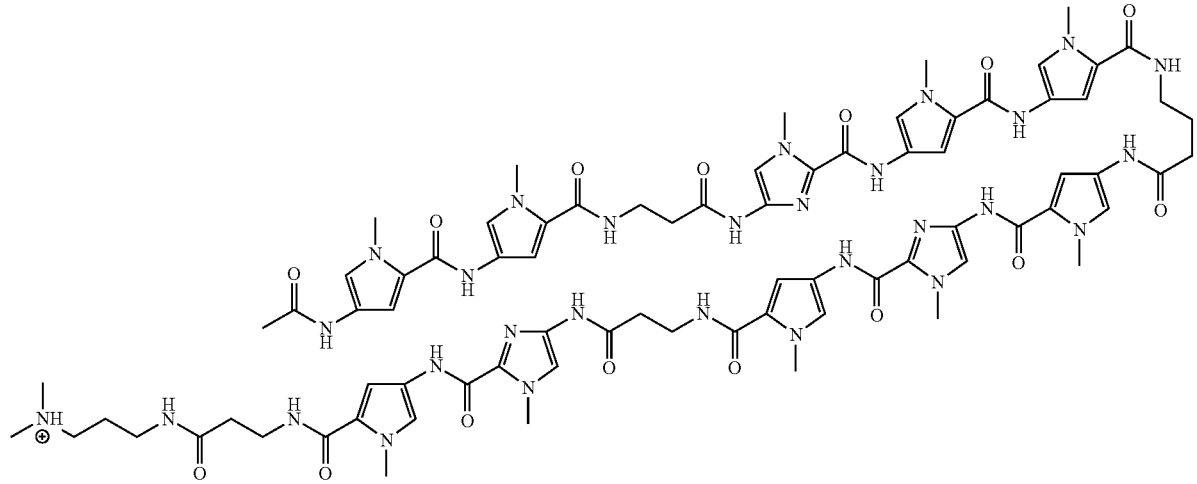

[Formula 2]

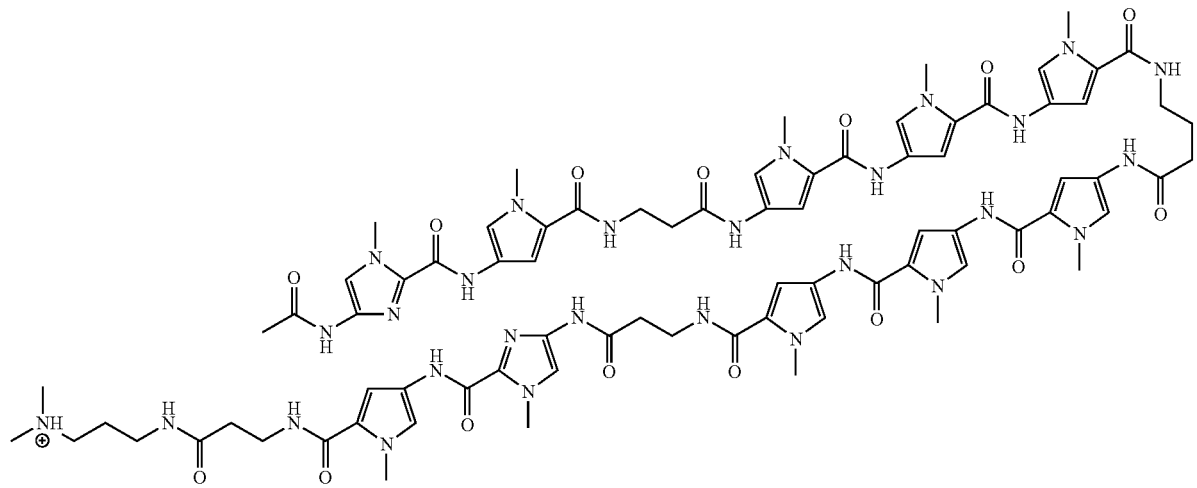

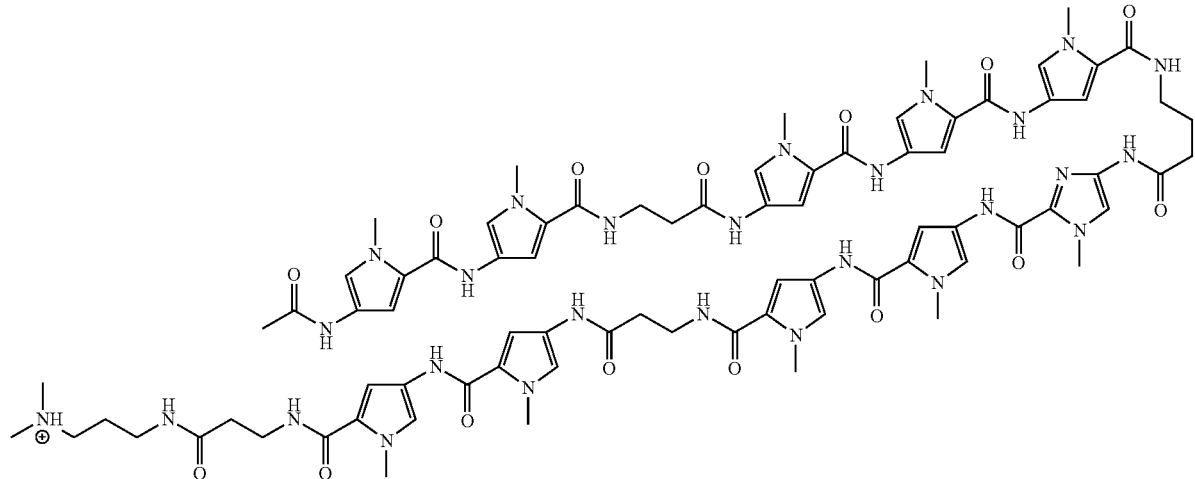

[Formula 3]

(3) An ACSL3 gene expression inhibitor containing the pyrrole-imidazole polyamide of (1) or (2) as an active ingredient.

(4) A preventive or therapeutic agent of prostate cancer containing the pyrrole-imidazole polyamide of (1) or (2) as an active ingredient.

Advantageous Effects of Invention

The provision of the PI polyamide of the present invention facilitates development of a safe and stable medicine useful for prevention and treatment of prostate cancer. The medicine contains as an active ingredient the PI polyamide of the present invention having high in-vivo stability and high transferability to tissues and cells and therefore may be an effective medicine for prevention and treatment of prostate cancer.

By combining with the PI polyamide developed by the present inventors inhibiting expression of a fusion gene between an androgen response gene TMPRSS2 and an ERG gene in an ETS family that is a transcriptional regulator (Japanese Patent Application No. 2012-106382), the PI polyamide also enables the comprehensive treatment etc. of prostate cancer.

DESCRIPTION OF EMBODIMENTS

A "PI polyamide" of the present invention includes any PI polyamide recognizing and binding to the whole or a portion of a base sequence indicated by SEQ ID NO:1.

The "portion" or "a part of" refers to recognition of at least one or more bases, preferably two or more bases, more preferably three or more bases in the base sequence indicated by SEQ ID NO:1 and a larger number of recognized bases is more preferable. If a plurality of bases is recognized, the recognized bases may be contiguous or may not be contiguous.

Figure 1:
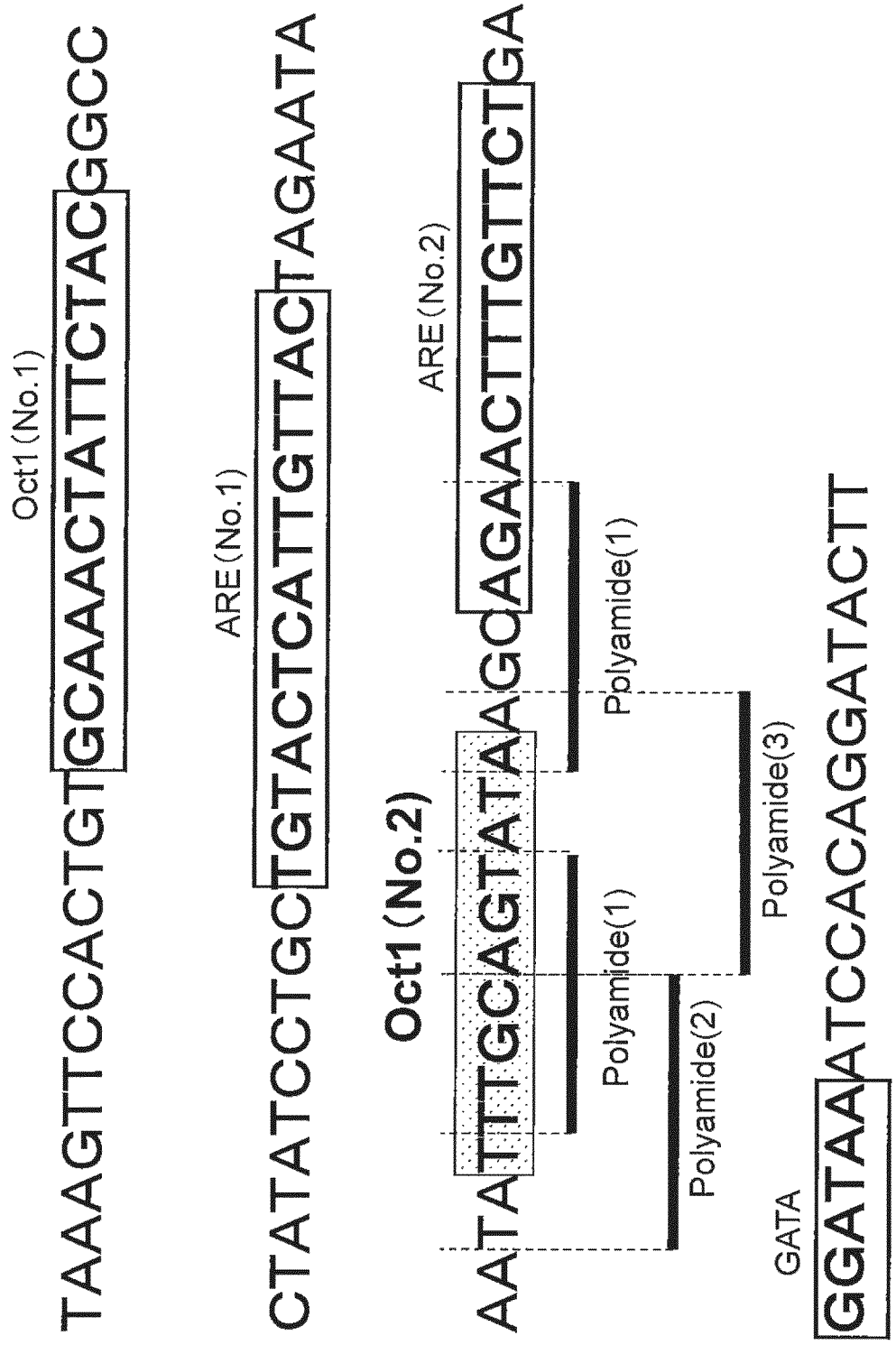
FIG. 1 is a schematic of base sequences of Oct1 gene binding sequences (OCT1 (No. 1), OCT1 (No. 2)), AREs (ARE (No. 1), ARE (No. 2)), and a GATA gene binding sequence (GATA) in a transcriptional regulatory region (AR response region) of an ACSL3 gene and PI polyamide binding sites (Polyamide (1) to Polyamide (3)) for the whole or a part of the base sequence of the Oct1 gene binding sequence (OCT1 (No. 2)).

With regard to the base sequence indicated by SEQ ID NO:1, as depicted in FIG. 1, the PI polyamide preferably recognizes and binds to the whole or a portion of a base sequence of an Oct1 gene binding sequence (OCT1 (No. 2))

between ARE (ARE (No. 1)) and ARE (ARE (No. 2)) in a transcriptional regulatory region (AR response region) of an ACSL3 gene.

The PI polyamide of the present invention may be any PI polyamide recognizing and binding to the whole or a portion of the base sequence indicated by SEQ ID NO:1 or may be a PI polyamide recognizing and binding to the whole or a portion of a base sequence complementary to the base sequence indicated by SEQ ID NO:1.

Moreover, since the PI polyamide has an Im/Py pair recognizing G-C in DNA, a Py/Im pair recognizing G-C, and a Py/Py pair recognizing T-A and A-T, the PI polyamide of the present invention may recognize and bind to the whole or a portion of a base sequence having G and C interchanged with each other at one or more locations or a base sequence having T and A interchanged with each other at one or more locations in the base sequence indicated by SEQ ID NO:1.

Such a "PI polyamide" of the present invention can be a PI polyamide (1), a PI polyamide (2), and a PI polyamide (3) represented by the following Formula 1, Formula 2, and Formula 3, respectively. FIG. 1 schematically depicts binding sites to the whole or a portion of the base sequence of the Oct1 gene binding sequence in these PI polyamides. The "PI polyamide" of the present invention is not limited to these PI polyamides represented by Formulas 1 to 3, may be any "PI polyamide" having the characteristics as described above, and includes a "PI polyamide" uniquely designed and produced with a conventionally known method.

[Formula 1]

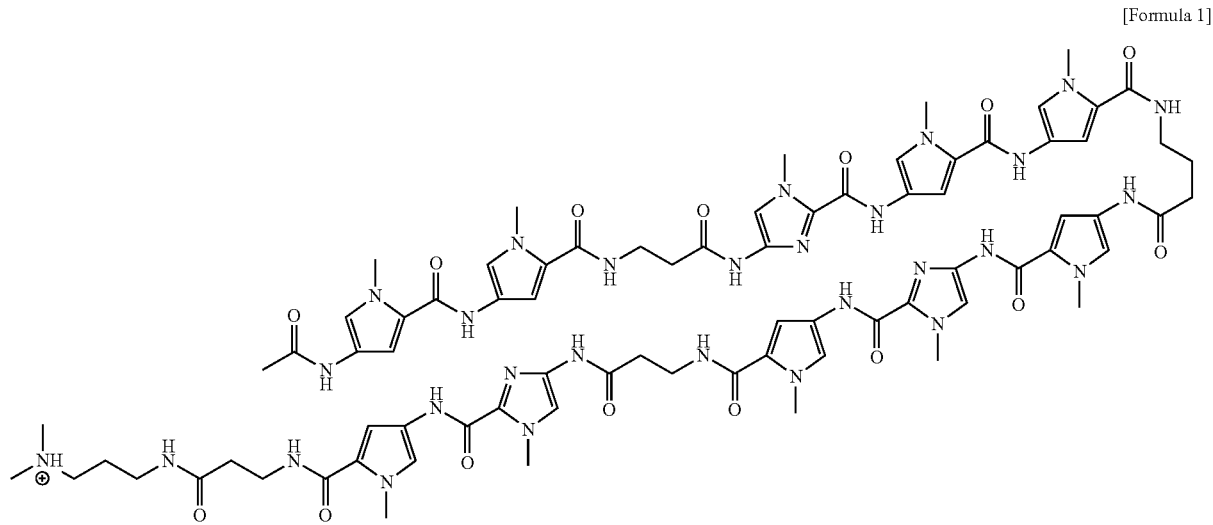

[Formula 2]

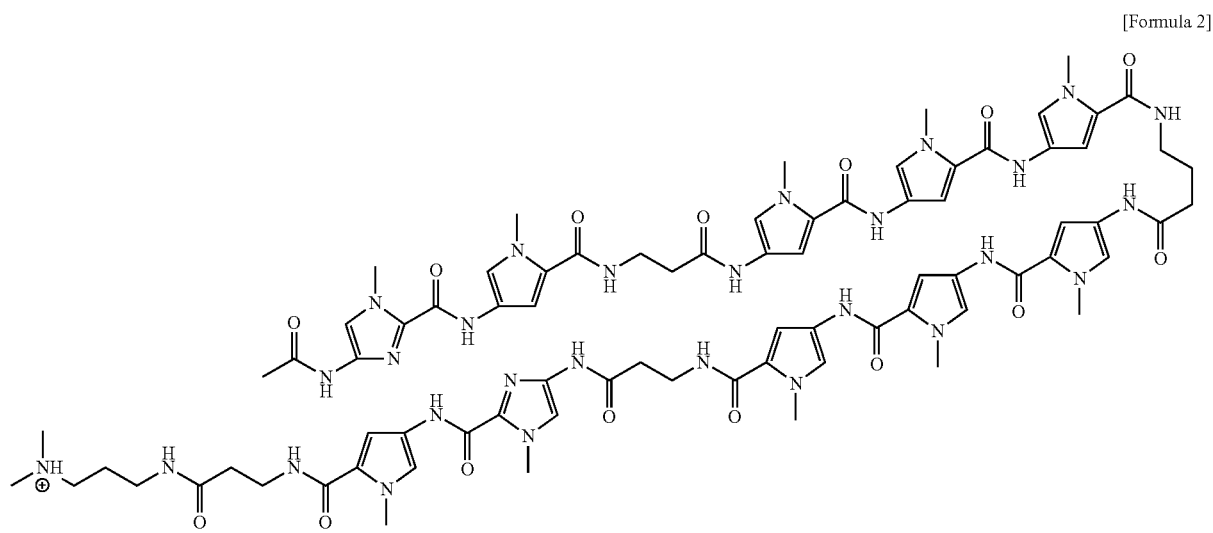

-continued

[Formula 3]

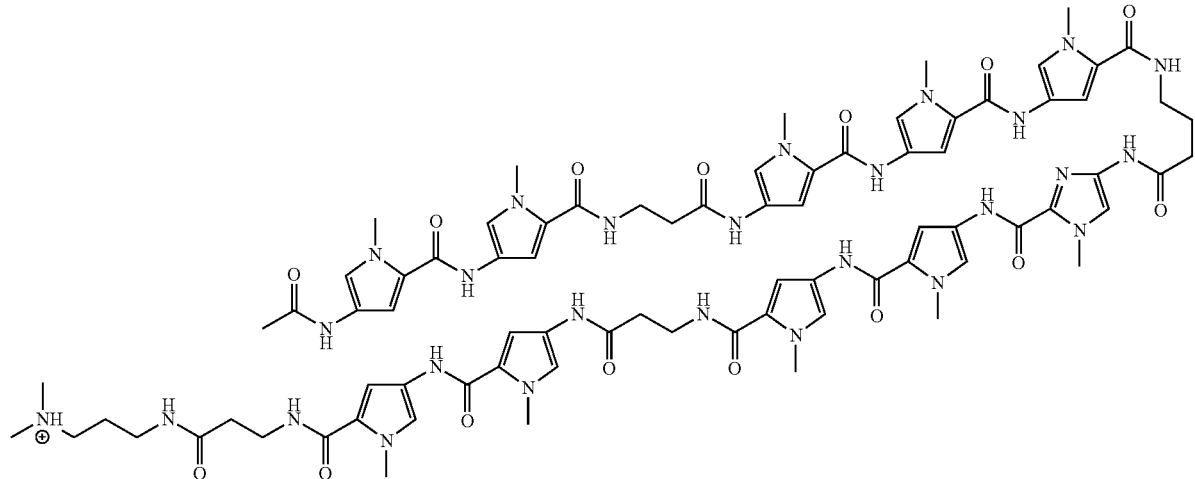

An "ACSL3 gene expression inhibitor" of the present invention refers to an agent containing the PI polyamide of the present invention as an active ingredient and binding to the whole or a portion of the Oct1 gene binding sequence to inhibit the expression of the ACSL3 gene.

The "expression inhibition" refers to a state of a reduced degree of the expression of the ACSL3 gene when the expression inhibitor of the present invention is applied to a cell in which the "expression of the ACSL3 gene" occurs such as a prostate cancer cell, as compared to when the expression inhibitor of the present invention is not applied. The reduced degree of the expression of the ACSL3 gene includes no expression of the ACSL3 gene.

Such an "ACSL3 gene expression inhibitor" of the present invention may be any agent containing the PI polyamide of the present invention as an active ingredient and may be an agent composed only of the PI polyamide of the present invention or an agent additionally containing a pharmaceutically acceptable component etc.

A "preventive and/or therapeutic agent of prostate cancer" of the present invention refers to an agent containing the PI polyamide of the present invention as an active ingredient and useful for prevention of prostate cancer, for treatment of prostate cancer, or for prevention and treatment of prostate cancer.

Such a "preventive and/or therapeutic agent of prostate cancer" of the present invention may be any agent containing the PI polyamide of the present invention as an active ingredient and may be an agent composed only of the PI polyamide of the present invention or an agent additionally containing a pharmaceutically acceptable component etc.

Such an agent of the present invention can be administered to a human likely to develop prostate cancer or can be administered after development of prostate cancer for the purpose of inhibiting the progression of the cancer or achieving the remission of the cancer.

The "preventive and/or therapeutic agent of prostate cancer" of the present invention can be used in combination with conventionally known medicines for prevention, treatment, etc. of prostate cancer or the PI polyamide developed by the present inventors inhibiting expression of a fusion gene between an androgen response gene TMPRSS2 and an ERG gene in an ETS family that is a transcriptional regulator (Japanese Patent Application No. 2012-106382).

Although the present invention will hereinafter be described in more detail by using an example and test examples, the present invention is not limited thereto.

EXAMPLE

Production of PI Polyamide

1. Design of PI Polyamide

The following PI polyamide (1), PI polyamide (2), and PI polyamide (3) were designed such that each binds to the whole or a portion of the Oct1 gene binding sequence (SEQ ID NO:1). For comparison, a PI polyamide (control) was also designed that does not bind to the whole or a portion of the Oct1 gene binding sequence (SEQ ID NO:1).

FIG. 1 depicts the binding sites of the PI polyamide (1), the PI polyamide (2), and the PI polyamide (3). Although the two binding sites of the PI polyamide (1) are depicted in FIG. 1, the PI polyamides (1) do not bind to the two sites at the same time since polyamides binding to the same gene must be separated by four or more bases from each other.

The letters in the following formulas have the following meaning:

Ac: acetyl, Py: pyrrole, Im: imidazole, β: β-alanine, γ: γ-butyrate, and Dp: N,N-dimethyl-1,3-propanediamine.

PI Polyamide (1)

API polyamide of AcPyPyβImPyPyγPyImPyβImPyβDp was designed to recognize the base sequence indicated by polyamide (1) in FIG. 1 (PI polyamide (1), Table 1) as a target base sequence. This PI polyamide is represented by the following formula (Formula 1) and has the chemical formula $C_{77}H_{96}N_{29}O_{15}^{+}$ and the molecular weight of 1667.77.

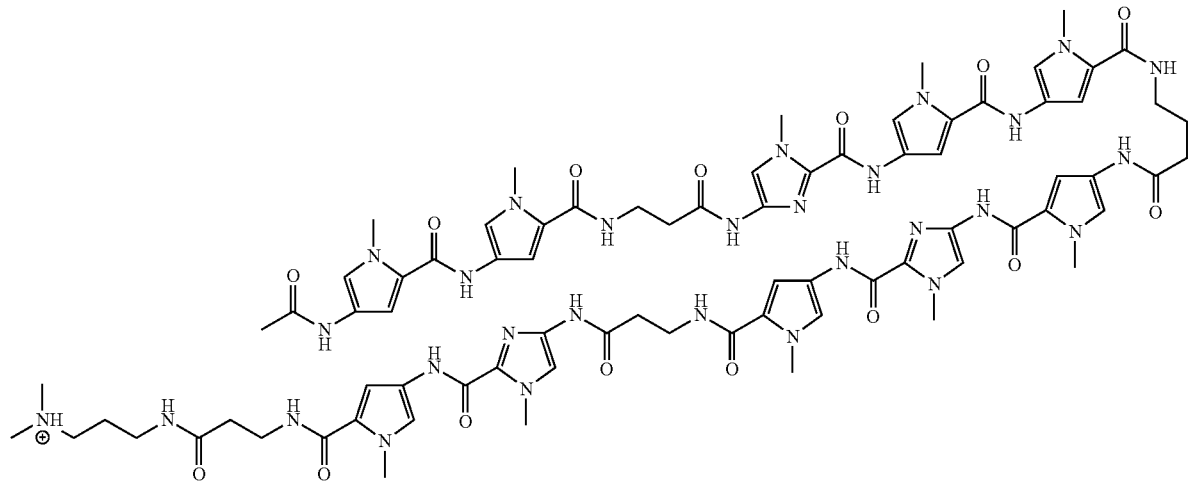

[Formula 1]

PI Polyamide (2)

API polyamide of AcImPyβPyPyPyγPyPyPyβImPyβDp was designed to recognize the base sequence indicated by polyamide (2) in FIG. 1 (PI polyamide (2), Table 1) as a target base sequence. This PI polyamide is represented by the following formula (Formula 2) and has the chemical formula $C_{78}H_{97}N_{28}O_{15}^{+}$ and the molecular weight of 1666.78.

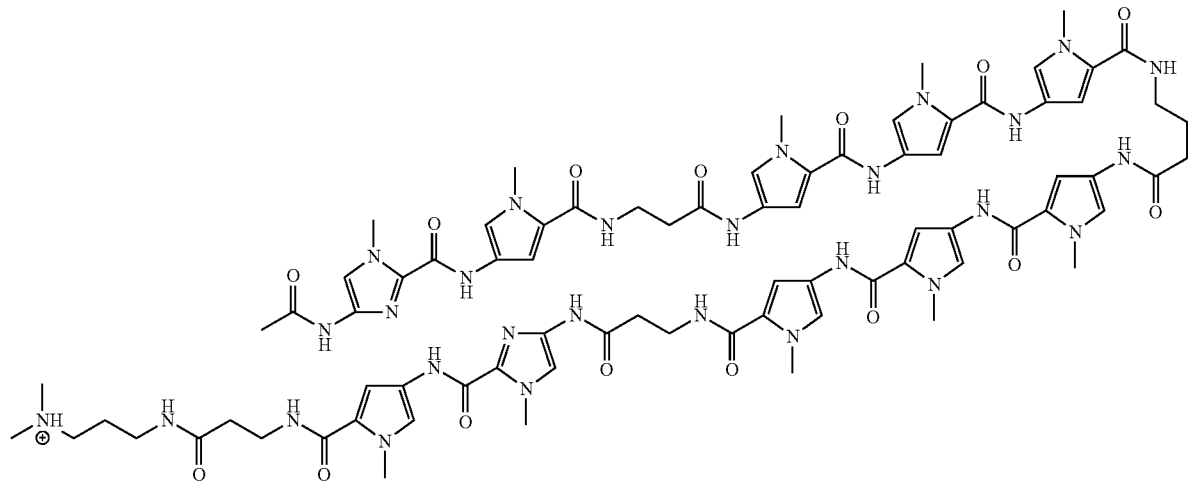

[Formula 2]

PI Polyamide (3)

API polyamide of AcPyPyβPyPyPyγImPyPyβPyPyβDp was designed to recognize the base sequence indicated by polyamide (3) in FIG. 1 (PI polyamide (3), Table 1) as a target base sequence. This PI polyamide is represented by the following formula (Formula 3) and has the chemical formula $C_{79}H_{98}N_{27}O_{15}^{+}$ and the molecular weight of 1665.79.

[Formula 3]

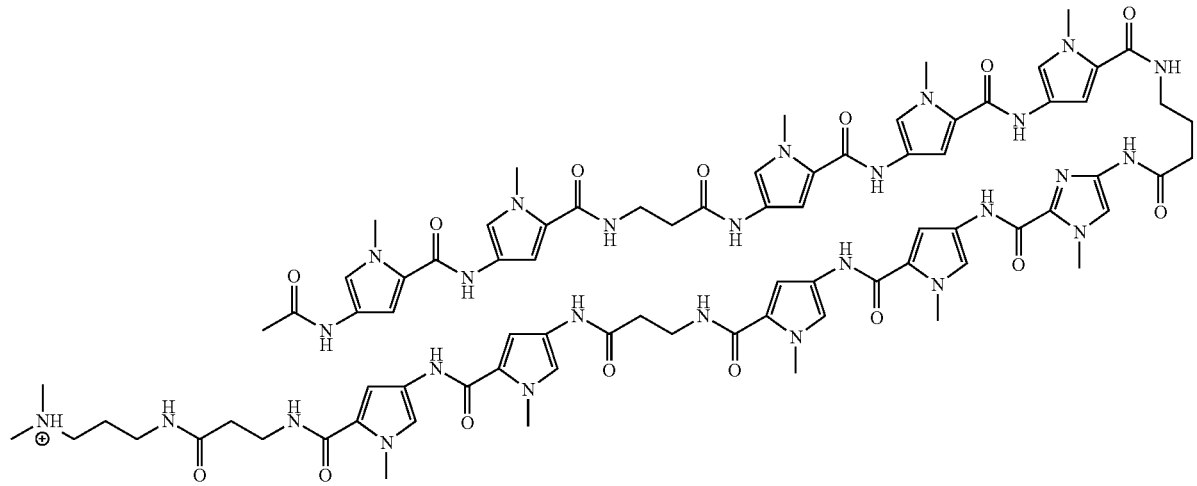

PI Polyamide (Control)

For the PI polyamide (control) not binding to the whole or a portion of the Oct1 gene binding sequence (SEQ ID NO:1), a PI polyamide of AcPyPyPyImβImγPyβPyImβImβDp was designed to recognize a base sequence indicated by PI polyamide (control) in Table 1 as a target base sequence. This PI polyamide is represented by the following formula (Formula 4) and has the chemical formula $C_{73}H_{94}N_{29}O_{15}{}^{+}$ and the molecular weight of 1617.71.

TABLE 1

| PI polyamide | Target base sequence | Sequence number |
|---|---|---|
| PI polyamide (1) | 5'-wwgcwgw-3' | 2 |
| | 3'-wwcgwcw-5' | 3 |
| PI polyamide (2) | 5'-wwwwwgc-3' | 4 |
| | 3'-wwwwwcg-5' | 5 |
| PI polyamide (3) | 5'-wgwwwww-3' | 6 |
| | 3'-wcwwwww-5' | 7 |

TABLE 1 -continued

| PI polyamide | Target base sequence | Sequence number |
|---|---|---|
| PI polyamide (control) | 5'-wcwcgwgw-3' | 8 |
| | 3'-wgwgcwcw-5' | 9 | w = A or T

2. Synthesis of PI Polyamide

[Formula 4]

<Synthesis of Pyrrole-Imidazole Polyamide Using HCTU>

HCTU (manufactured by Peptide Institute, Inc.) was used as a condensation activating agent to synthesize each of the PI polyamides (1) to (3) (three types) and the PI polyamide (control) designed in 1.

1) Preparation of Reagents
(1) Monomers

FmocPyCOOH (20 mg, Wako), FmocImCOOH (40 mg, Wako), Fmoc-γ-Abu-OH (17.5 mg, Nova Biochem), and Fmoc-β-Ala-OH (17.5 mg, Nova Biochem) were prepared in an amount necessary for coupling of each of the PI polyamides to be synthesized, and 2 equivalents of FmocImCOOH and 4 equivalents of each of the others to resin were weighed and each transferred to a 1.5 mL Eppendorf tube. Additionally, 45 mg and 22.5 mg of HCTU were added to the tube of FmocImCOOH and each of the other tubes, respectively. Moreover, 500 µL and 250 µL of NMP (manufactured by Nacalai tesque) were added to the tube of FmocImCOOH and each of the other tubes, respectively, and vortexed and allowed to stand still for 1 hour for complete dissolution.

(2) Reagents for Synthesis

Reagents listed in Table 2 were prepared and used for synthesis by a synthesizer.

TABLE 2

Necessary Reagents for Synthesizer per Sample

| | | |
|---|---|---|
| Activater (condensing reagent) | DIEA(N,N-diisopropylethylamine) | 3 mL |
| Deblock (for Fmoc group deprotection) | 30% Piperidine/DMF Piperidine NMP | 7.5 mL 17.5 mL |
| Wash (solvent for washing) | NMP | 200 mL |

3. Preparation of Resin

Forty mg (0.04 mmol) of Fmoc-β-Ala-Wang-Resin (manufactured by Peptide Institute) was put into a Small Libra Tube (manufactured by HiPep Laboratories) and set in a peptide synthesizer. Addition of 1 mL of NMP was followed by 20 minutes of swelling.

4. Peptide Synthesis (Automated)

DIEA prepared in 1. was installed as a condensation activating agent in the synthesizer (PSSM-8 manufactured by Shimadzu Corporation). The tubes containing the monomers prepared earlier were arranged in a rack in the synthesizer in the order from the C-terminal. After setting a synthesis program of PSSM-8, the synthesizer was started to perform automatic synthesis by repeating the following reaction cycle from (1) to (4) until H$_2$NAcPyPyβImPyPyγPyImPyβImPyβ-Resin, H$_2$NAcImPyβPyPyPyγPyPyPyβImPyβ-Resin, H$_2$NAcPyPyβPyPyPyγImPyPyβPyPyβ-Resin, or H$_2$NAcPyPyPyImβImγPyβPyImβImβ-Resin.

Reaction Cycle (1) A coupling process was performed by using the activating agent in NMP for 30 minutes.

(2) To remove excessive monomers and activating agent, the resin was repeatedly washed five times with 1 mL of NMP.

(3) 1 ml of an Fmoc deprotection solution (30% Piperidine/NMP) was added and reacted for 3 minutes and the same cycle was repeated again after removing the solution.

(4) To remove the Fmoc deprotection solution, the resin was repeatedly washed five times with 1 mL of NMP before returning to (1). This cycle was repeated until a target product was acquired.

5. Purification

The resin was taken out form the synthesizer, washed, dried and then transferred to an Eppendorf tube with a screw cap. After 500 µL of N,N-dimethylpropanediamine (2 mL, manufactured by Nacalai tesque) was added, the resin was heated by a heat block at 55° C. overnight to cut out a polyimide from the resin. The reaction solution was transferred to a Libra tube to remove the resin through filtration, and a remaining reaction solution adhering to the resin was collected with 1 mL of NMP and 1 mL of methanol.

After solvent was distilled away, fractionation and purification were performed by HPLC (0.1% AcOH:CH3CN=100:0 to 0:100, 30 min). After the fractionation and purification, each of the PI polyamides (1) to (3) (three types) and the PI polyamide (control) designed in 1. was acquired through freeze dehydration.

6. DNA Binding Assay

For each of the PI polyamides (1) to (3) (three types) generated in 5, a DNA Binding Assay of the following steps 1) and 2) was performed to confirm binding to the Oct1 gene binding sequence (SEQ ID NO:1). The PI polyamide (control) was also examined in terms of the presence/absence of binding to the Oct1 gene binding sequence (SEQ ID NO:1).

1) Molecules (50-base) were created that have Oct1 oligo DNA including the same base sequence as the Oct1 gene binding sequence (SEQ ID NO:1) labelled with FITC, and the oligo at a final concentration of 1 µM was heated to 100° C. in an annealing buffer (20 mM Tris-HCl, 2 mM EDTA, 200 mM NaCl). The oligo was cooled for 2 hours in stages to 30° C. As a result, the Oct1 oligo DNA underwent self-annealing and forms a double strand in a hairpin shape.

2) 15 µl of solution containing the hairpin-shaped double strand DNA of 1) was mixed with 5 µl of each of the 0.2 mM PI polyamides (1) to (3) and PI polyamide (control) and incubated at 37° C. for 1 hour to acquire a mixed solution.

3) The mixed solution of 2) was electrophoresed in 5-20% acrylamide gel (TBE buffer) and an electrophoretic pattern was monitored with LAS 4000 (manufactured by GE Healthcare Japan) to determine the presence/absence of binding from a difference in the electrophoretic pattern.

4) As a result, it was confirmed that all the PI polyamides (1) to (3) of the present invention bind to the Oct1 oligo DNA, while no binding occurs in the case of the PI polyamide (control) or only a solvent without the PI polyamide.

Test Examples

The following test examples 1 to 6 were used for confirming the effect of the PI polyamide of the present invention to a prostate cancer cell (LNCaP) and a tumor. For common samples in the test examples, the following samples were prepared in the same way and used.

<Samples>

1. PI Polyamide

The PI polyamides (1) to (3) (tree types) and the PI polyamide (control) synthesized in the same way as the example were used.

These PI polyamides are dissolved in distilled water and added to a cell culturing medium for introduction into cells.

2. Prostate Cancer Cell LNCaP

Human prostate cancer cells LNCaP (ATCC No. CRL-174) acquired from ATCC (American Type Culture Collection) were used.

3. Medium (1) Phenol-Red-Containing Medium

A Phenol-Red-containing medium used was 500 mL of Phenol-Red-containing RPMI-1640 medium (manufactured by SIGMA-Aldrich, catalogue No. R7509) to which 50 ml of charcoal-treated fetal bovine serum (FBS) was added.

(2) Phenol-Red-Free Medium

A Phenol-Red-free medium used was 500 mL of Phenol-Red-free RPMI-1640 medium (manufactured by SIGMA-Aldrich, catalogue No. R8758) to which 12.5 ml of charcoal-treated fetal bovine serum (FBS) was added.

4. DHT (dehydrotestosterone) (Wako Junyaku)

DHT dissolved in ethanol (EtOH) to 100 nM was used for androgen stimulation.

Test Example 1

Evaluation of AR Activity in ACSL3 Transcriptional Regulatory Region (AR Response Region)

An influence on AR activity was examined in the case of mutation or deletion in each of the following base sequences in the ACSL3 transcriptional regulatory region (AR response region):
1) Oct1 gene binding sequences (OCT1 (No. 1), OCT1 (No. 2), FIG. 1),
2) AREs (ARE (No. 1), ARE (No. 2), FIG. 1), and
3) GATA gene binding sequence (GATA, FIG. 1).

1. PCR

About 1 kb of AR binding site (ARBS) located 63 kb upstream of the ACSL3 transcription start point was extracted (SEQ ID NO:10) and used as template DNA to amplify the following mutated ARBSs (1) to (5) with PCR:
(1) ARBS with OCT1 (No. 1) deleted (by using a primer Mut Oct #1 of Table 3);
(2) ARBS with OCT1 (No. 2) deleted (by using a primer Mut Oct #2 of Table 3);
(3) ARBS with GATA deleted (by using a primer Mut GATA of Table 3);
(4) ARBS with OCT1 (No. 2) deleted and ARE (No. 1) mutated (by using primers Mut Oct #2 and Mut ARE 1 of Table 3); and
(5) ARBS with Oct1 (No. 2) deleted and ARE (No. 1) and ARE (No. 2) mutated (by using primers Mut Oct #2, Mut ARE 1, and Mut ARE 2 of Table 3).

The mutated ARBSs were acquired through the following procedures.
(1) To the template DNA (SEQ ID NO:10), PCR was performed by using a primer for a gene desired to be mutated or deleted as a forward primer and a primer for the terminal end of the template DNA (ACSL3 ARBS rv primer of Table 3) as a reverse primer to acquire an amplified construct.
(2) To the template DNA (SEQ ID NO:10), PCR was performed by using a primer for the leading end of the template DNA (ACSL3 ARBS fw primer of Table 3) as a forward primer and a primer for a gene desired to be mutated or deleted as a reverse primer to acquire an amplified construct.
(3) To a template DNA acquired by mixing the constructs acquired at (1) and (2), PCR was performed by using the primer for the leading end of the template DNA (ACSL3 ARBS fw primer of Table 3) as a forward primer and the primer for the terminal end of the template DNA (ACSL3 ARBS rv primer of Table 3) as a reverse primer to acquire the mutated ARBSs.

TABLE 3

| primer name | base sequence of primer (5'-3') | sequence number |
|---|---|---|
| ACSL3 ARBSfw | AAAACGCGTGGCATAGTATATCTGTGGGACATTC | 11 |
| ACSL3 ARBSrv | TGAAGATCTTGATTATTGGGTATTGTGGGAGCAG | 12 |
| Mut ARE 1 | TGTAATCATTATTACTAGAATAAATATTTGCA | 13 |
| Mut ARE 2 | AGAAATTTATTCTGAGGATAAATCCACA | 14 |

TABLE 3 -continued

| primer name | base sequence of primer (5'-3') | sequence number |
|---|---|---|
| Mut Oct #1 | TAAAGTTCCACTGTGGCCCTATATC | 15 |
| Mut Oct #2 | TAGAATAAATAAGCAGAACTTTGTTCT | 16 |
| Mut GATA | AGCAGAACTTTGTTCTCAGGATACTT | 17 |

2. Luciferase Assay

Each of the mutant ARBSs of (1) to (5) was inserted into a luciferase vector (pGL3 promoter vector: Promega, Madison, Wis.) and used for transfection of a prostate cancer cell (LNCaP) cultured for about 60 hours in the Phenol-Red-free medium of 3. (2) Using FuGENE (registered trademark) HD (Roche Applied Science) as a transection reagent in accordance with the protocol thereof.

After about 12 hours, R1881 (NEN Life Science Products) was used for applying androgen stimulation and, after another 24 hours, a luciferase assay was performed. In this test, a prostate cancer cell (LNCaP) incorporated with the ARBS without deletion or mutation (template DNA, SEQ ID NO:10) was used as a positive control for the luciferase vector.

Figure 2:
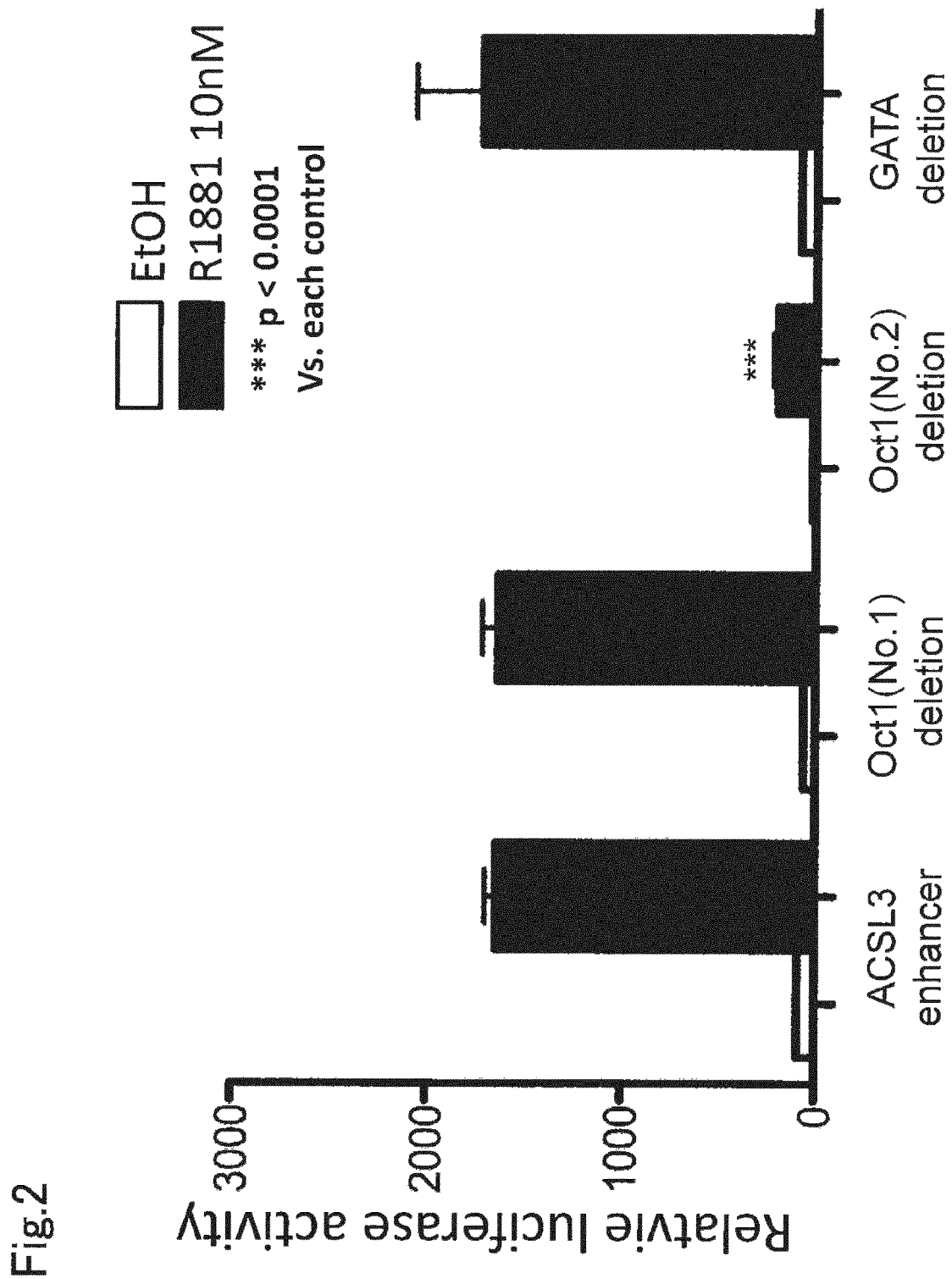
FIG. 2 is a diagram of an evaluation result of AR activity in the ACSL3 transcriptional regulatory region (AR response region) (test example 1).

As a result, as depicted in FIG. 2, it was confirmed that (1) ARBS with OCT1 (No. 1) deleted (Oct1 (No. 1) deletion of FIG. 2) and (3) ARBS with GATA deleted (GATA deletion, FIG. 2) exhibited the AR activity similar to the positive control (ACSL3 Enhancer, FIG. 2) while (2) ARBS with OCT1 (No. 2) deleted (Oct1 (No. 2) deletion, FIG. 2) had significantly reduced AR activity.

Figure 3:
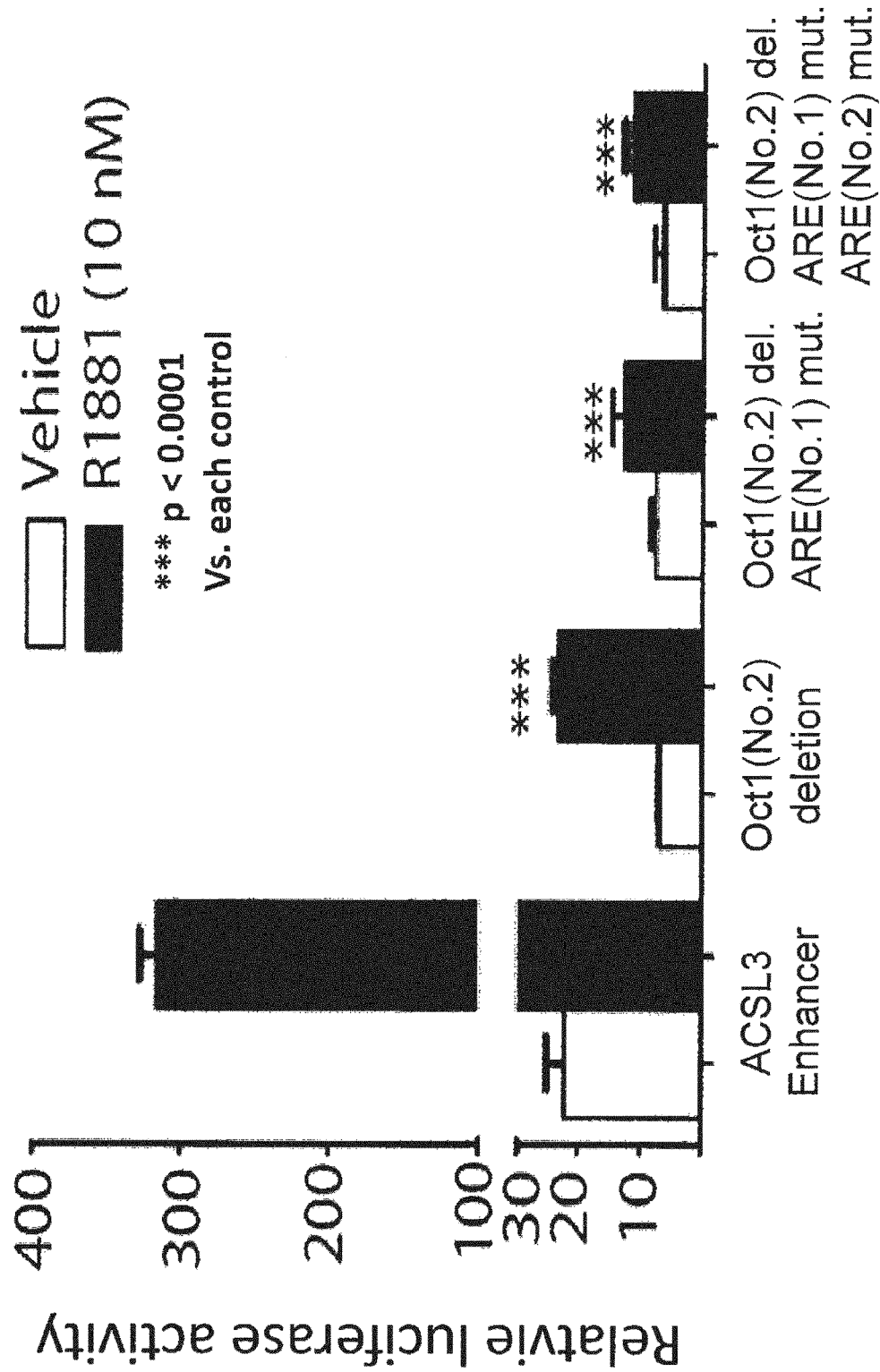
FIG. 3 is a diagram of an evaluation result of AR activity in the ACSL3 transcriptional regulatory region (AR response region) (test example 1).

As depicted in FIG. 3, it was confirmed that the AR activity was significantly reduced as compared to the positive control (ACSL3 Enhancer, FIG. 3) in each of the cases of (2) ARBS with OCT1 (No. 2) deleted (Oct1 (No. 2) deletion, FIG. 3), (4) ARBS with OCT1 (No. 2) deleted and ARE (No. 1) mutated (Oct1 (No. 2) del. ARE (No. 1) mut., FIG. 3), and (5) ARBS with Oct1 (No. 2) deleted and ARE (No. 1) and ARE (No. 2) mutated (Oct1 (No. 2) del. ARE (No. 1) mut. ARE (No. 2) mut., FIG. 3).

Therefore, this result indicated that the action of Oct1 (No. 2) in the Oct1 gene binding sequence is important for the AR activity in the ACSL3 transcriptional regulatory region (AR response region).

Test Example 2

Examination of Expression of ACSL3 Gene

The expression of ACSL3 Gene was examined by RT-PCR in a cell into which each of the PI polyamides (1) to (3) was introduced. For comparison, the same examination was conducted for a cell into which the PI polyamide (control) was introduced.

1) Introduction of PI Polyamide and Preparation of cDNA

The LNCaP cells were cultured for 3 days in the Phenol-Red-free medium of 3. (2) to which each of the PI polyamides was added at 5 µM. Subsequently, DHT (100 nM) of 4. was added into the medium to apply androgen stimulation.

After RNA is extracted from the cells by using Isogen (Nippon Gene) in accordance with a manual, cDNA was prepared by using PrimeScript (registered trademark) Reverse Transcriptase (manufactured by TaKaRa).

2) RT-PCR

Each of the cDNAs prepared in 1) was used as a template DNA to examine with primers listed in Table 4 the presence/absence of expression of a fusion gene or an ERG gene in the prostate cancer cell into which each of the PI polyamides was introduced. In this RT-qPCR, Power SYBR (registered trademark) Green PCR Master Mix (manufactured by Applied Biosystems) was used.

TABLE 4

| amplification object | base sequence of primer (5'-3') | sequence number |
|---|---|---|
| ACSL3 gene | GCACAGGCGTGTTTTATGTATAATTT | 18 |
| | CAATGGCTGGACCTCCTAGAGT | 19 |
| GAPDH gene (internal standard) | GGTGGTCTCCTCTGACTTCAACA | 20 |
| | GTGGTCGTTGAGGGCAATG | 21 |

Figure 4:
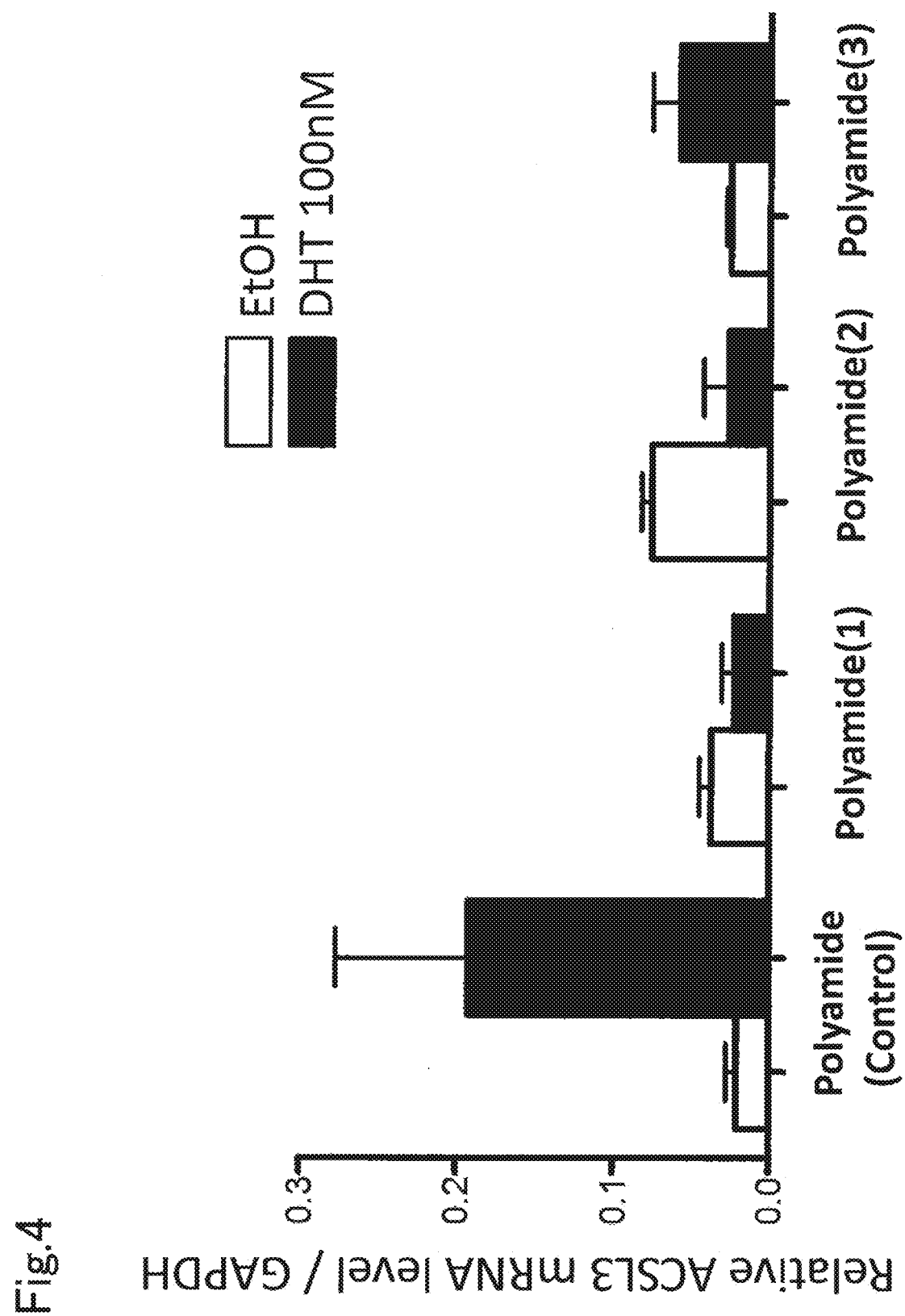
FIG. 4 is a diagram of a result of expression of the ACSL3 genes in prostate cancer cells treatment with these PI polyamides (test example 2).

As a result, as depicted in FIG. 4, it was confirmed that the expression of the ACSL3 gene was inhibited in the cells treatment with the PI polyamide (1), PI polyamide (2), or PI polyamide (3) even when the androgen stimulation was applied. In contrast, the expression of the ACSL3 gene was not inhibited in the cell treatment with the PI polyamide (control) (Polyamide (Control), FIG. 4).

Figure 5:
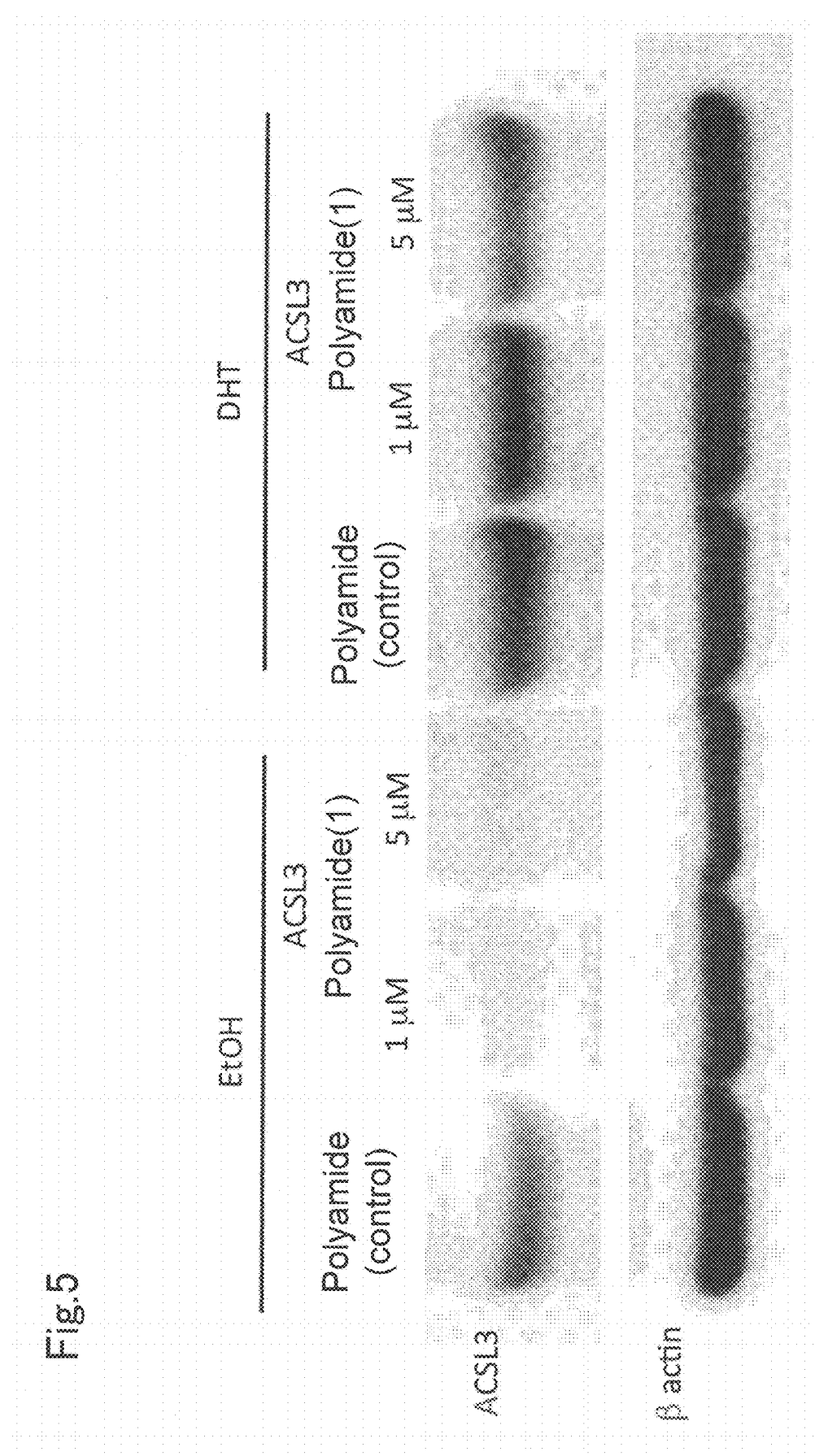
FIG. 5 is a diagram of a result of expression of the ACSL3 gene in prostate cancer cells treatment with 1 µM or 5 µM of the PI polyamide (1) (test example 2).

FIG. 5 depicts a result of ACSL3 gene expression inhibition in the cell treatment with 1 µM or 5 µM of the PI polyamide (1), and it was confirmed that the expression of the ACSL3 gene was particularly inhibited in the cells treatment with 5 µM of the PI polyamide (1), when the androgen stimulation was applied.

Test Example 3

Evaluation of AR Activity in ACSL3 Transcriptional Regulatory Region (AR Response Region)

About 1 kb of AR binding site (ARBS) located 63 kb upstream of the ACSL3 transcription start point was extracted (SEQ ID NO:10) and insert into a luciferase vector (pGL3 promoter vector: Promega, Madison, Wis.). This vector was used for transfection of a prostate cancer cell (LNCaP) cultured for about 60 hours in the Phenol-Red-free medium of 3. (2) by using FuGENE (registered trademark) HD (Roche Applied Science) as a transection reagent in accordance with the protocol thereof.

After about 12 hours, androgen stimulation using 100 nM of DHT and introduction of the PI polyamide (1) or PI polyamide (control) (1 µM or 5 µM) were performed and followed by a luciferase assay. This test was conducted by using prostate cancer cells (LNCaP) incorporated with a PSA promoter region (SEQ ID NO:22) known to have AR response activity as a positive control for the luciferase vector.

Figure 6:
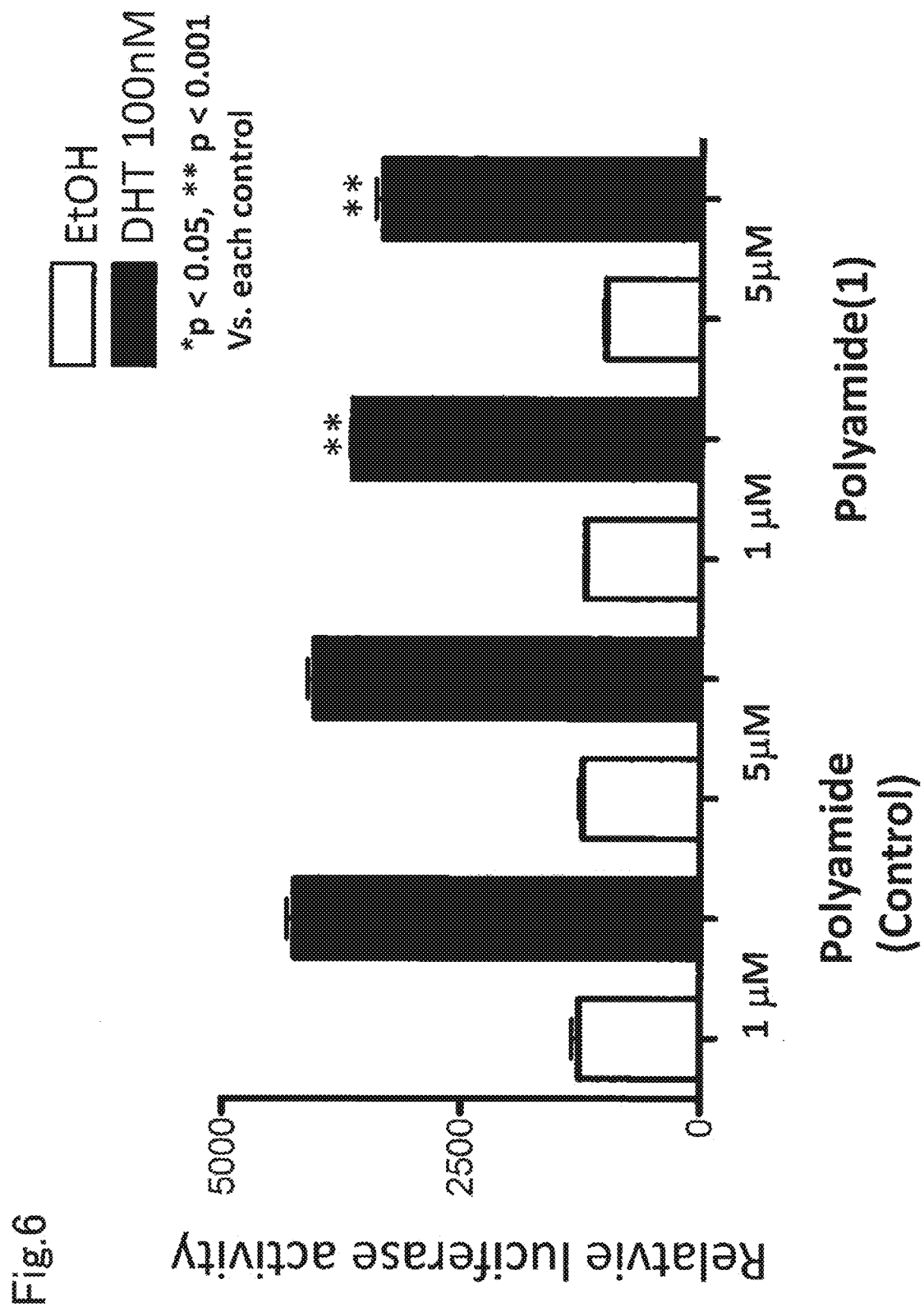
FIG. 6 is a diagram of a result of AR activity in the ACSL3 transcriptional regulatory region (AR response region) for prostate cancer cells treatment with these PI polyamides (test example 3).

As a result, as depicted in FIG. 6, it was confirmed that the introduction of the PI polyamide (1) significantly reduces the AR activity in the ACSL3 transcriptional regulatory region (AR response region) as compared to the introduction of the same amount of the PI polyamide (control). The same applied to the cases of using the PI polyamide (2) and the PI polyamide (3).

Figure 7:
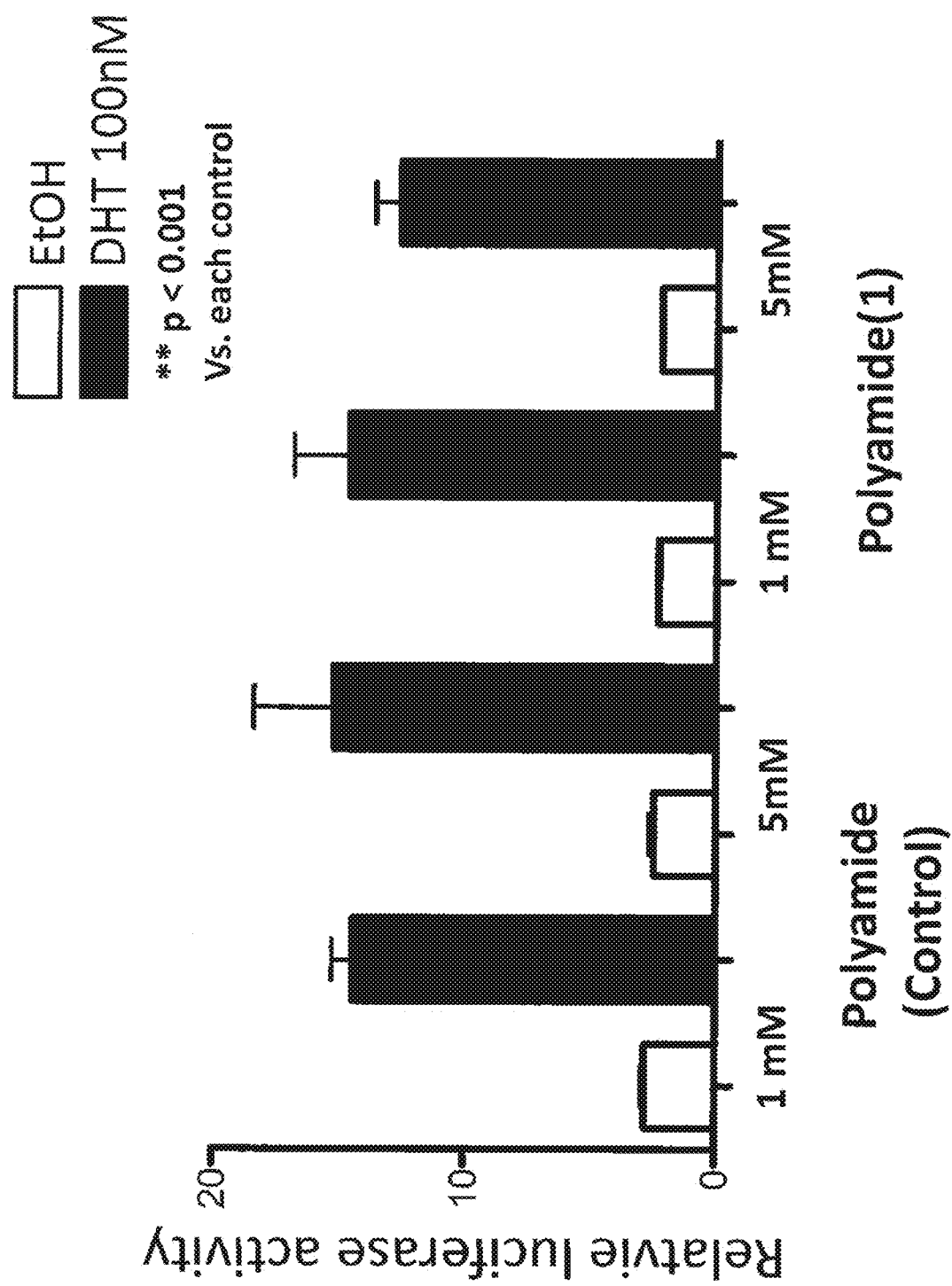
FIG. 7 is a diagram of a result of AR activity in the PSA promoter region (AR response region) as a positive control) for prostate cancer cells treatment with these PI polyamides (test example 3).

As depicted in FIG. 7, it was confirmed that when the prostate cancer cells (LNCaP) incorporated with the PSA promoter region as the positive control were used, no significant difference existed between the introduction of the PI polyamide (1) and the introduction of the same amount of the PI polyamide (control).

Test Example 4

Evaluation of Proliferation Ability

After treatment with the PI polyamide (1) or the PI polyamide (control) for comparison, the proliferation ability of these cells were examined by MTS assay.

In particular, the LNCaP cells were seeded on a 96-well plate to $5 \times 10^3$ cells in total and cultured for 3 days in the Phenol-Red-free medium of 3. (2) to which each of the PI polyamides was added at 1 µM or 5 µM. Subsequently, DHT (100 nM) of 4. was added into the medium to apply androgen stimulation. After the stimulation, each of the cells were cultured for 24, 48, or 96 hours.

After the specified stimulation time, 10 µl of an MTS reagent (Cell Titer 96 AQueous One Solution Cell Proliferation Assay, Promega, Madison Wis.) was added to the cells before incubation for 1 hour. Subsequently, the absorbance (490 nm) of the cells was measured and the numbers of the cultured cells were examined to evaluate the cell proliferation ability.

Figure 8:
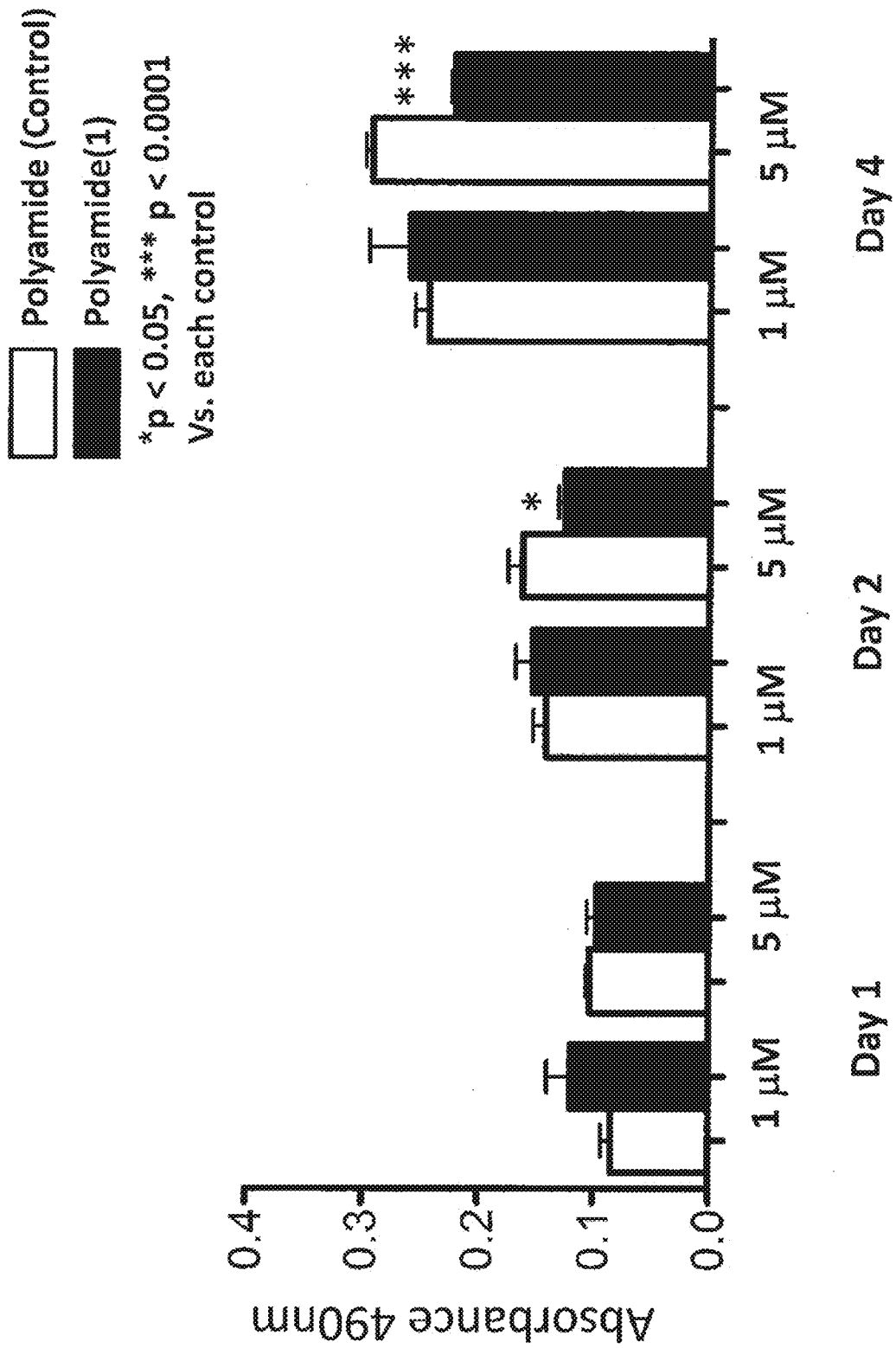
FIG. 8 is a diagram of the result of cell proliferation ability of prostate cancer cells treatment with these PI polyamides (test example 4).

As a result, as depicted in FIG. 8, it was confirmed that the proliferation was significantly inhibited in the cell treatment with 5 µM of the PI polyamide (1) (FIG. 8) after 48 hours of incubation as compared to the cell treatment with PI polyamide (control, 5 µM, FIG. 8) and that the proliferation was further significantly inhibited after 96 hours of incubation. The cell proliferation was suppressed in the same way when the PI polyamide (2) and the PI polyamide (3) were used.

Test Example 5

Evaluation of Cell Migration Ability

After culturing cells into which the PI polyamide (1) was introduced and cells into which the PI polyamide (control) was introduced for comparison, the migration ability of the cells was examined by a cell migration assay using a cell culture insert and a 8.0 µm pore size PET filter (manufactured by Becton Dickinson).

In particular, after fibronectin (manufactured by Sigma) diluted with PBS to 10 µg/ml was allowed to act on a culture dish for 30 minutes to form a lower filter, 700 µl of the Phenol-Red-containing RPMI 1640 medium of 3. (1) was added to a lower chamber.

The LNCaP cells were cultured for 3 days in the Phenol-Red-containing medium of 3. (1) to which each of the PI polyamides was added at 5 µM and divided into units of $5 \times 10^4$ cells, and each unit of cells was suspended in 300 µl of the Phenol-Red-containing medium of 3. (1) and added to the upper chamber. After the cells were cultured at 37° C. under the condition of 5% $CO_2$, the filter was peeled off.

The cells on the lower filter were fixed by methanol for 30 minutes and then incubated for 30 seconds in Gimsa's stain solution (manufactured by Muto Pure Chemicals). Subsequently, the cells were observed by a microscope of 200 magnifications to count the number of cells, thereby evaluating the cell migration ability.

Figure 9:
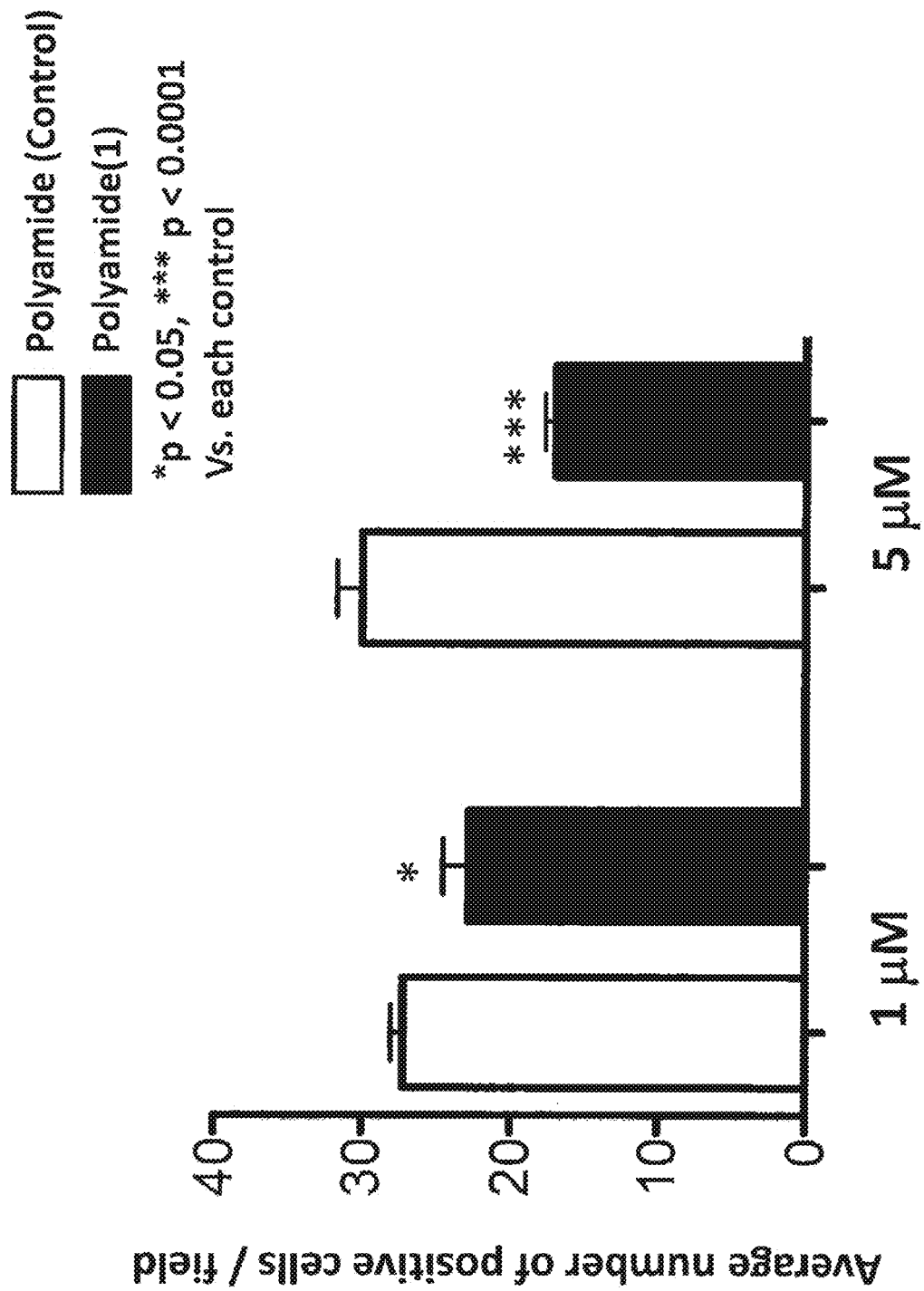
FIG. 9 is a diagram of confirmation of the result of cell migration ability for prostate cancer cells treatment with these PI polyamides (test example 5).
Figure 10:
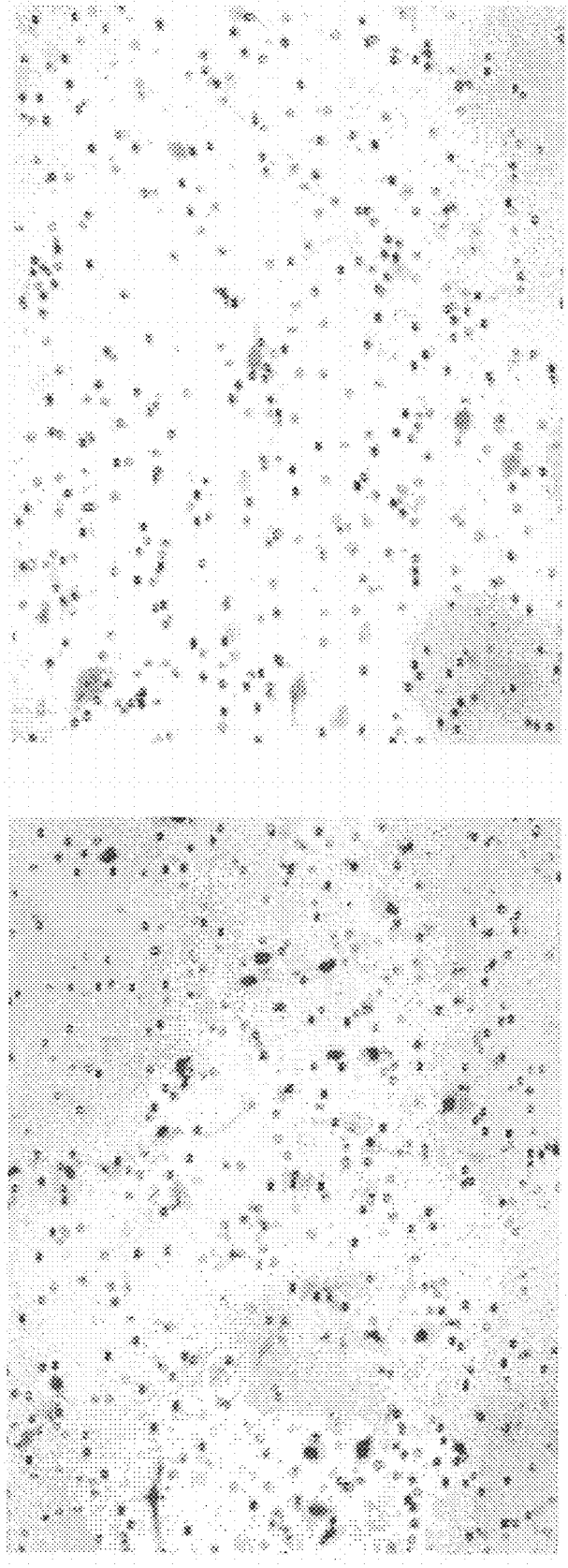
FIG. 10 is a diagram of microscope photographs of cells treatment with the PI polyamides which was introduced in the evaluation of cell migration ability (test example 5).

FIG. 9 depicts the numbers of migrated cells to which the PI polyamides were added. FIG. 10 depicts microscope photographs of the cells to which the PI polyamides were added.

As a result, as depicted in FIGS. 9 and 10, it was confirmed that the cell migration ability (invasive potential) was significantly inhibited in the cell into which the PI polyamide (1) of the present invention was introduced (Polyamide (1), FIGS. 9 and 10) as compared to the cell into which the PI polyamide (control) was introduced (Polyamide (control), FIGS. 9 and 10). The cell migration ability (invasive potential) was suppressed in the same way with respect to the PI polyamide (2) and the PI polyamide (3).

Test Example 6

The effect of the PI polyamide on a tumor was confirmed.

To 7-week-old male nude mice (n=10), $3 \times 10^6$ prostate cancer cells (LNCaP) were subcutaneously injected at the right flank. A tumor size was monitored by caliper measurement every 3 days. When the tumor size reaches 100 cm$^2$, the PI polyamide (1) or the PI polyamide (control) dissolved in dH$_2$O was injected from a tail vein at 6 mg/kg bodyweight (PI polyamide (1): n=4, PI polyamide (control): n=6).

The injection was performed once per week for 4 weeks and the tumor size was measured every week. After one week from the last injection, the nude mice were dissected to excise the tumors.

Figure 11:
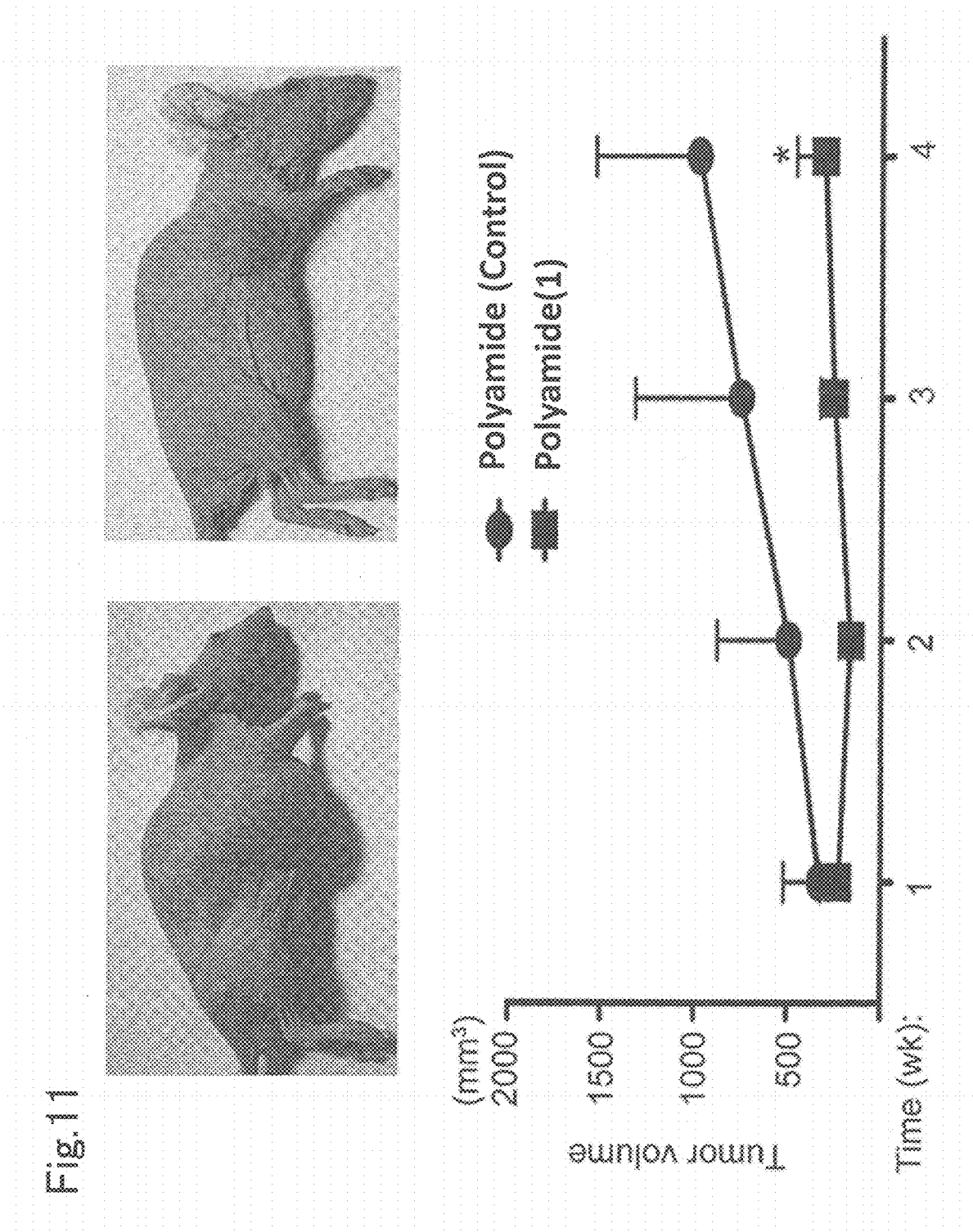
FIG. 11 is a diagram of an effect of the PI polyamide to a tumor (test example 6).

As a result, as depicted in FIG. 11, it was confirmed that the formation of tumor was remarkably inhibited in the nude mice subjected to the injection of the PI polyamide (1) as compared to the nude mice subjected to the injection of the PI polyamide (control).

Figure 12:
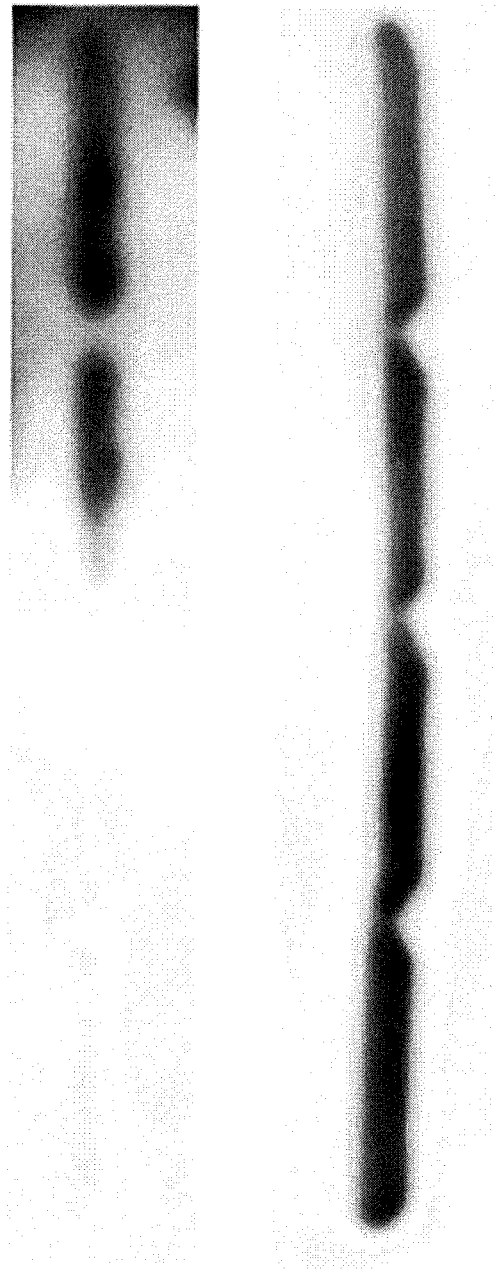
FIG. 12 is a diagram of an expression inhibition effect of the PI polyamide to an ACSL3 protein derived from LNCaP cells injected into nude mice (test example 6).

FIG. 12 depicts a result of western blotting with an ACSL3 antibody of protein extracted using a lysis buffer (NP40 buffer) from the excised tumors (two individuals #1 and #2) (upper portion of FIG. 12; lower portion indicates expression of β-actin protein). As a result, it was confirmed that the ACSL3 protein was expressed in the nude mice subjected to the injection of the PI polyamide (control) while the expression of the ACSL3 protein was remarkably inhibited in each of the nude mice subjected to the injection of the PI polyamide (1).

INDUSTRIAL APPLICABILITY

The provision of the PI polyamide of the present invention facilitates the development of a safe and stable medicine useful for prevention and treatment of prostate cancer. By combining with the PI polyamide developed by the present inventors inhibiting expression of a fusion gene between an androgen response gene TMPRSS2 and an ERG gene in an ETS family that is a transcriptional regulator (Japanese Patent Application No. 2012-106382), the PI polyamide also enables the comprehensive treatment etc. of prostate cancer.

The invention claimed is:

1. A pyrrole-imidazole polyamide binding to the whole or a part of a base sequence comprising SEQ ID NO:1, the pyrrole-imidazole polyamide being represented by any of the following Formulas 1 to 3:

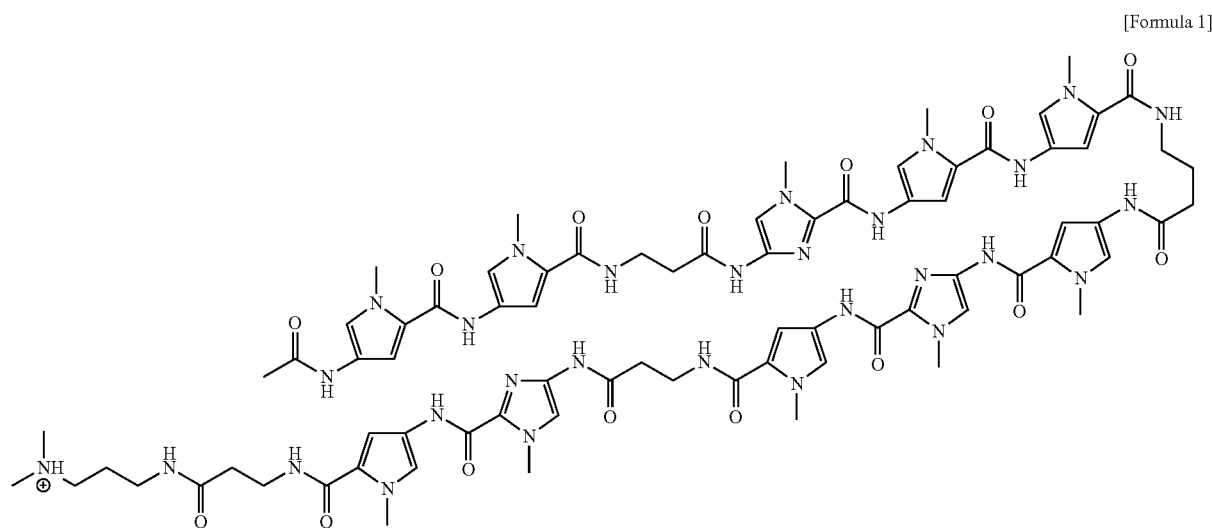 [SMILES: CC(=O)Nc1cc(C(=O)Nc2cc(C(=O)NCCC(=O)Nc3cc(C(=O)Nc4cc(C(=O)Nc5cc(C(=O)NCCCC(=O)Nc6cn(C)c(C(=O)Nc7cc(C(=O)Nc8cc(C(=O)NCCC(=O)Nc9cc(C(=O)Nc%10cc(C(=O)NCCC(=O)NCCC[NH+](C)C)n(C)c%10)n(C)c9)n(C)c8)n(C)c7)n6)n(C)c5)n(C)c4)n(C)c3)n(C)c2)n(C)c1]

[Formula 1]

[Formula 2]
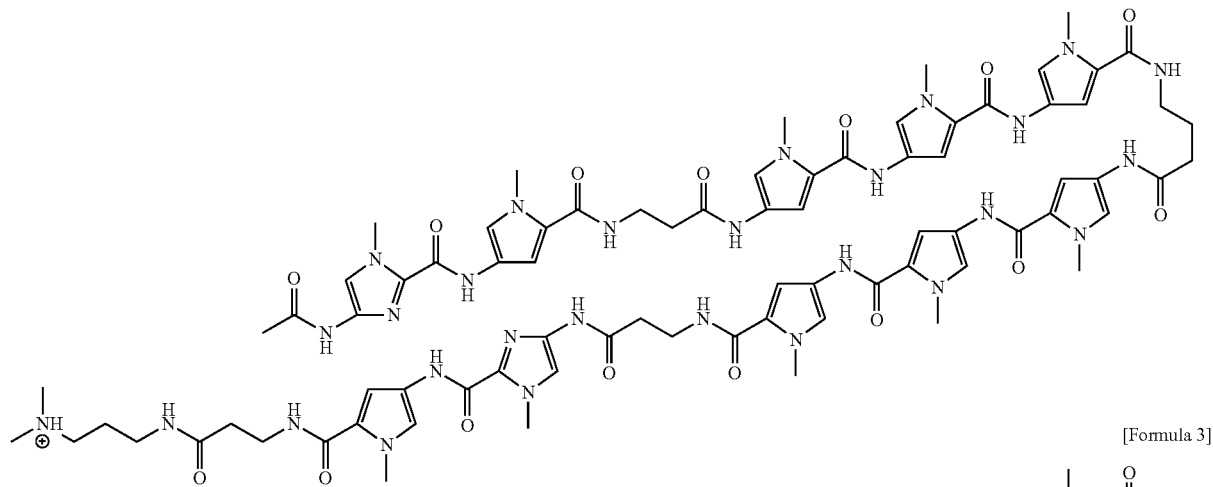
[Formula 3]
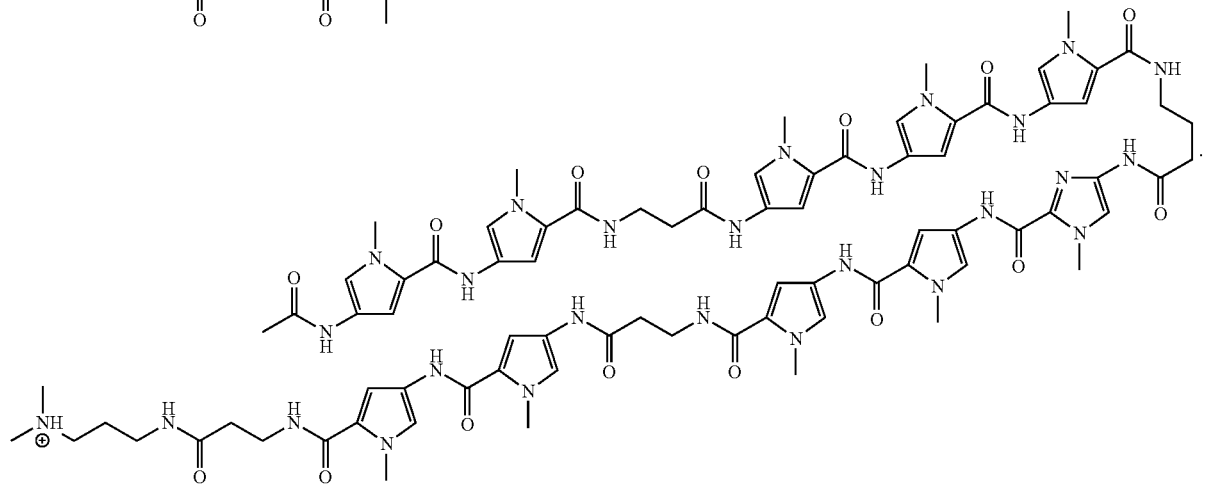
2. An ACSL3 gene expression inhibitor containing a pyrrole-imidazole polyamide represented by any of the following Formulas 1 to 3:
[Formula 1]
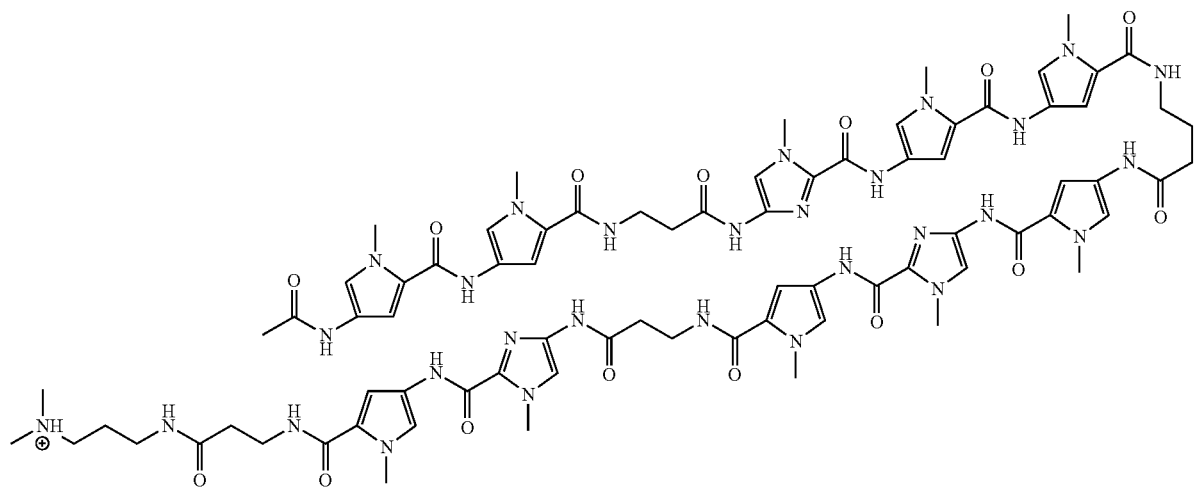

[Formula 2]
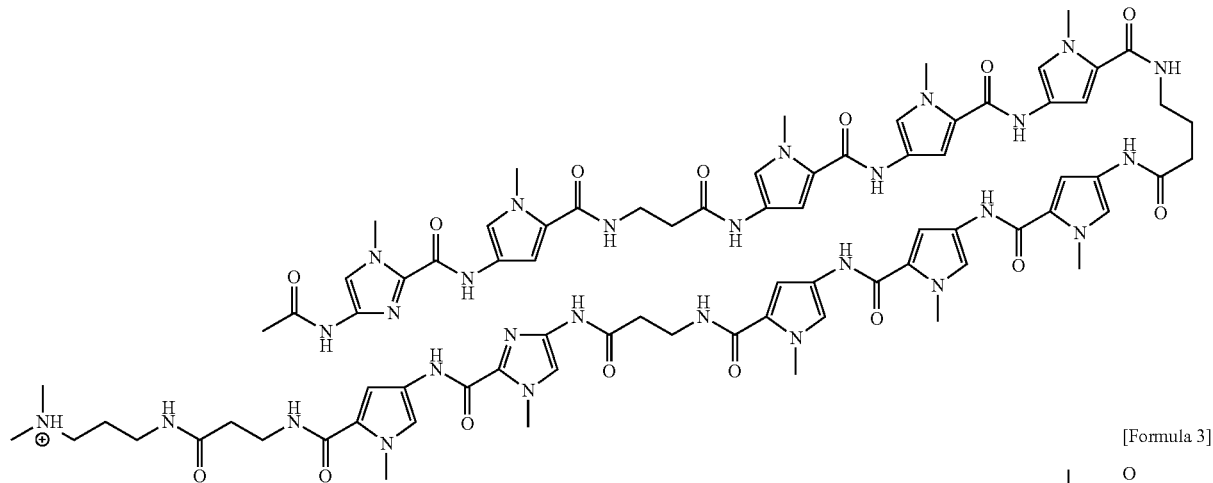
[Formula 3]
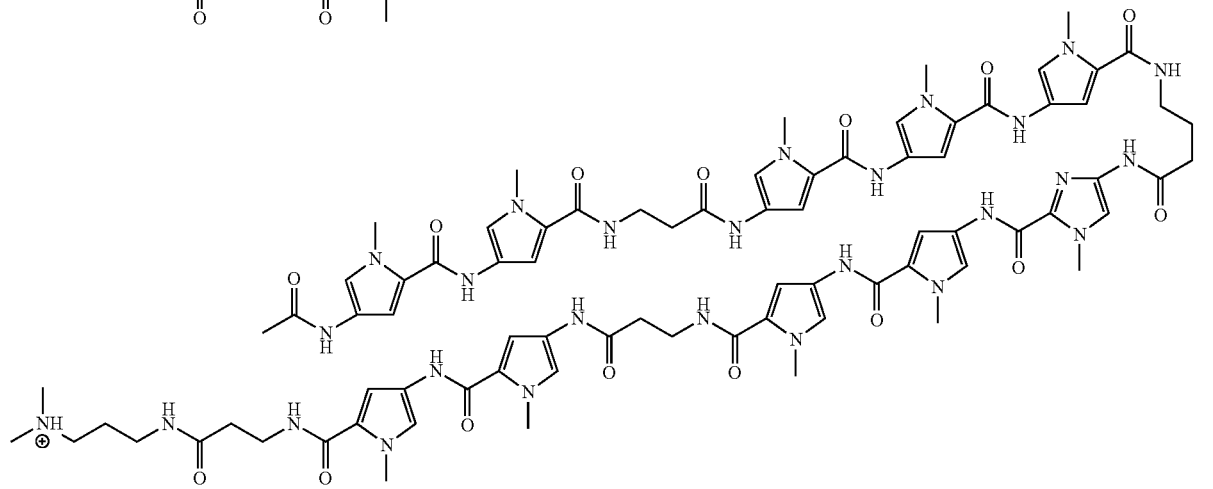
as an active ingredient.
3. A preventive or therapeutic agent of prostate cancer containing the pyrrole-imidazole polyamide represented by any of the following Formulas 1 to 3:
[Formula 1]
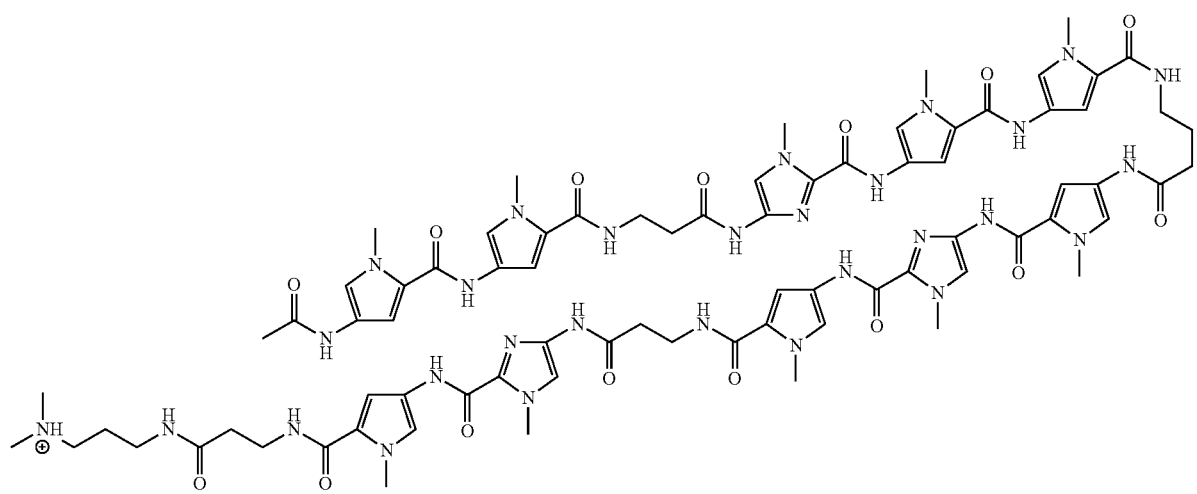

-continued
[Formula 2]
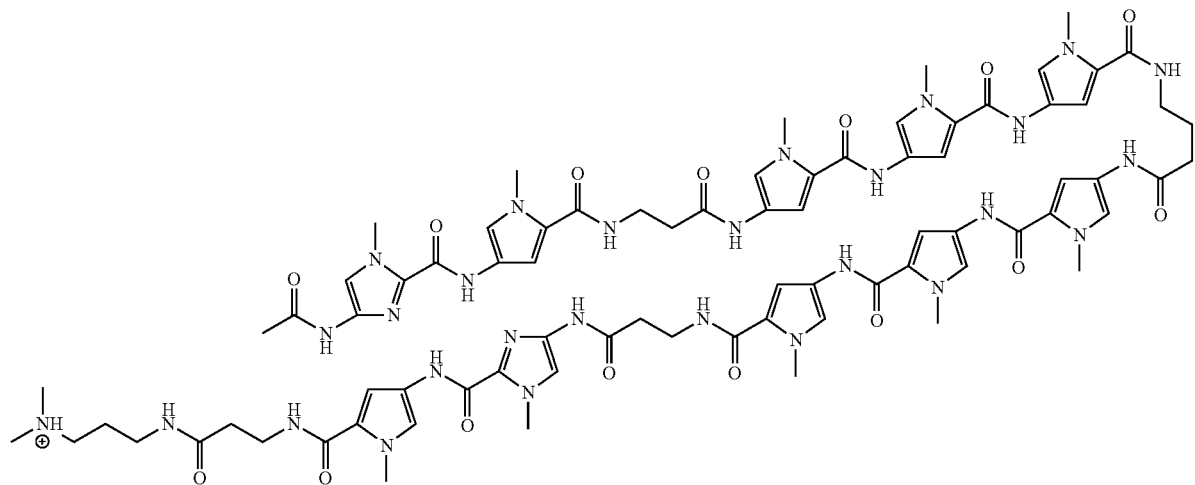
[Formula 3]
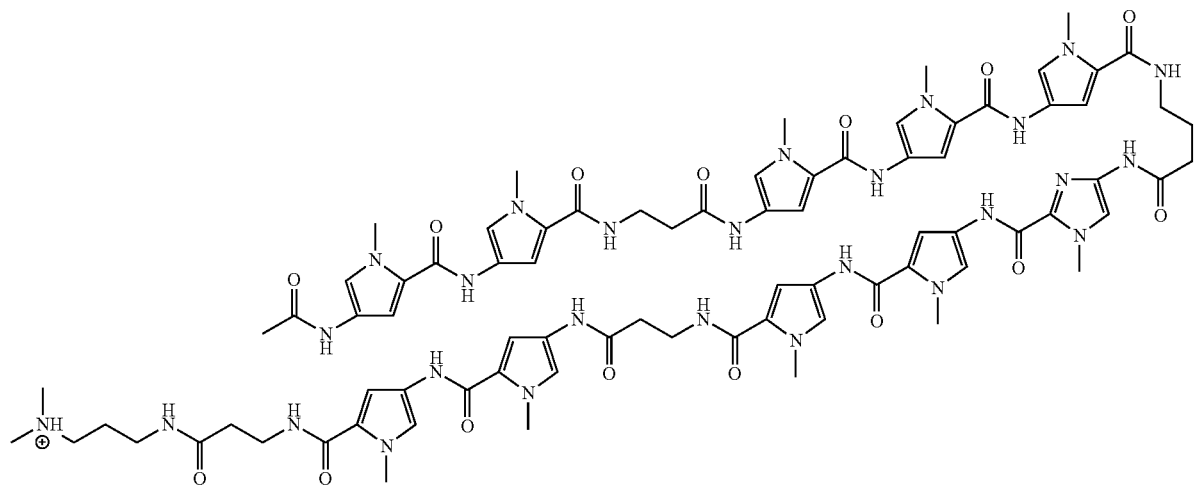
as an active ingredient.
* * * * *